United States Patent [19]

Little et al.

[11] Patent Number: 5,359,509
[45] Date of Patent: Oct. 25, 1994

[54] HEALTH CARE PAYMENT ADJUDICATION AND REVIEW SYSTEM

[75] Inventors: John P. Little, Minneapolis; R. Scott McMahon, Eden Prairie, both of Minn.; Mark Gingrich, Downingtown, Pa.; Roleigh H. Martin, Eden Prairie, Minn.

[73] Assignee: United Healthcare Corporation, Minneapolis, Minn.

[21] Appl. No.: 786,123

[22] Filed: Oct. 31, 1991

[51] Int. Cl.$^5$ .................. G06F 15/21; G06F 15/42
[52] U.S. Cl. ............................ 364/401; 364/406; 364/413.01; 395/924
[58] Field of Search .............. 364/401, 413.01, 406, 364/408; 395/924, 925

[56] References Cited

U.S. PATENT DOCUMENTS

| 4,667,292 | 5/1987 | Mohlenbrock et al. | 364/406 |
| 4,858,121 | 8/1989 | Barber et al. | 364/406 |
| 4,916,611 | 4/1990 | Doyle, Jr. et al. | 364/401 |
| 5,018,067 | 5/1991 | Mohlenbrock et al. | 364/413.02 |
| 5,070,452 | 12/1991 | Doyle, Jr. et al. | 364/401 |
| 5,136,502 | 8/1992 | Van Remortel et al. | 364/413.01 |
| 5,225,976 | 7/1993 | Tawil | 364/401 |
| 5,235,507 | 8/1993 | Sackler et al. | 364/401 |

OTHER PUBLICATIONS

Code Review, an expert system for correcting physician coding errors, Health Payment Review, Inc., Aug. 15, 1991.

*Primary Examiner*—Roy N. Envall, Jr.
*Assistant Examiner*—Jennifer L. Hazard
*Attorney, Agent, or Firm*—Patterson & Keough

[57] ABSTRACT

A computerized expert system reviews and adjudicates medical health care payment requests made by physicians to payers, such as insurers, for procedures performed and services and materials rendered to patients in the course of treatment. The system adjudicates a payment request to minimize fraud and mistakes and to determine whether to honor the request and if the request is honored, the dollar amount of the payment. The expert system reviews the payment request based on user-specified review criteria. Such criteria reflects contractual arrangements between payers, providers and patients, current, locally acceptable medical practices and patient and provider payment request patterns.

To perform the review, the expert system obtains relevant prior payment requests as necessary according to the user's pre-determined review criteria; defines a master list of payable payment requests given current medical procedures, the predetermined parameters of the review and specific contractual arrangements between the payer, patient and health care provider; analyses the current payment request according to the relevant historical payment requests and the master payable list by applying user-defined interpretive rules to this information; and develops and reports payment decisions based on that analysis.

10 Claims, 17 Drawing Sheets

Fig. 2a

| PATIENT'S NAME (LAST, FIRST, MI) | BIRTH DATE | SEX | RELATIONSHIP CODE | JOB CONNECTED ILLNESS OR INJURY | YES NO | OTHER INSURANCE COVERAGE | YES NO UNKNOWN |
|---|---|---|---|---|---|---|---|
| SMITH, JOHN P. | 6/8/88 | M | 1 SELF 2 SPOUSE 3 CHILD 4 OTHER | | ☐ ☑ | | 2 |

| INSURANCE NUMBERS (POLICY, GROUP, MEDICARE, ETC.) | REFERRING PHYSICIAN | NAME OF HOSPITAL, NURSING HOME, ETC. | IF ACCIDENT, GIVE DATE |
|---|---|---|---|
| A HEALTH PLAN 3456 | | MERCY | |

INDICATE NAME AND ADDRESS OF INSURANCE COMPANY
A HEALTH PLAN
123 Drive
City, State Zip Code I AUTHORIZE PAYMENT OF MEDICAL BENEFITS TO THE PHYSICIAN OR SUPPLIER FOR THE SERVICES DESCRIBED BELOW.

X _____ SIGNATURE _____ DATE

ABC PHYSICIANS, PA
RIDGE POINT MEDICAL BLDG
14050 NICOLLET AVE S SUITE
BURNSVILLE MN 55337

0085-01 SMITH, FRED
1234 SCOTT TERRACE
1SB  MPLS MN 55416

PROVIDER NAME AND ADDRESS
ATTENDING PHYSICIAN'S
STATEMENT FOR INSURANCE

YOUR ACCOUNT NUMBER: 100100    PAGE NUMBER: 1
PLEASE SHOW ON ALL CHECKS

| DATE | PATIENT NAME / EXPLANATION OF ACTIVITY | CPT4 CODE | ICD-9 CODE | DOCTOR NAME | CHARGES AND DEBITS | PAYMENT AND CREDITS |
|---|---|---|---|---|---|---|
| 100.19 15 | John Tonsillectomy/adenoidectomy | 042820 | | JONES | | |
| 100.19 15 | Adenoidectomy | 042830 | | JONES | | |
| 100.19 15 | Typanostomy (ear-tube) | 069436 | | JONES | | |
| 100.19 15 | Esophagotomy (chest) | 430458 0 | | JONES | | |

PROVIDER NOS: BCBS 12345FA    FED-ID 41-1234567

STATEMENT CLOSING DATE 10-31-91
NEW CHARGES

TO PATIENT: FILE THIS COPY WITH YOUR INSURANCE COMPANY ONLY IF CHARGES ARE LISTED.

ABC PHYSICIANS, PA
RIDGE POINT MEDICAL BLDG
14050 NICOLLET AVE S SUIT
BURNSVILLE MN 55337

TO INSURANCE CO.: SEE REVERSE SIDE FOR CODING.
PLEASE EXPEDITE PAYMENT AS YOUR INSURED WILL CONTINUE TO RECEIVE MONTHLY STATEMENTS UNTIL ACCOUNT IS PAID IN FULL.

*Fig. 2b*

| PATIENT'S NAME (LAST, FIRST, MI) | BIRTH DATE | SEX | RELATIONSHIP CODE | JOB CONNECTED ILLNESS OR INJURY | YES NO | OTHER INSURANCE COVERAGE | YES NO UNKNOWN |
|---|---|---|---|---|---|---|---|
| SMITH, JOHN P. | 6/8/88 | M | 1 SELF 2 SPOUSE 3 CHILD 4 OTHER | | ☐ ☒ | | 2 |
| INSURANCE NUMBERS (POLICY, GROUP, MEDICARE, ETC.) | REFERRING PHYSICIAN | | NAME OF HOSPITAL, NURSING HOME, ETC. | | IF ACCIDENT, GIVE DATE | | |
| A HEALTH PLAN 3456 | | | MERCY | | | | |

INDICATE NAME AND ADDRESS OF INSURANCE COMPANY

2 | A HEALTH PLAN
123 Drive
City, State Zip Code

3 | I AUTHORIZE PAYMENT OF MEDICAL BENEFITS TO THE PHYSICIAN OR SUPPLIER FOR THE SERVICES DESCRIBED BELOW.
X ___ SIGNATURE ___ DATE

54 — XYZ PHYSICIANS, PA
RIDGE POINT MEDICAL BLDG
14050 NICOLLET AVE S SUITE
BURNSVILLE MN 55337

0085-01    SMITH, FRED — 56
            1234 SCOTT TERRACE
1SB         MPLS MN 55416

PROVIDER NAME AND ADDRESS
ATTENDING PHYSICIAN'S
STATEMENT FOR INSURANCE

| YOUR ACCOUNT NUMBER | 200200 | PAGE NUMBER | 1 |

PLEASE SHOW ON ALL CHECKS

| DATE | PATIENT NAME EXPLANATION OF ACTIVITY | | CPT4 CODE | ICD-9 CODE | DOCTOR NAME | CHARGES AND DEBITS | PAYMENT AND CREDITS |
|---|---|---|---|---|---|---|---|
| 10 15 91 | John Esophagotomy (chest) | 5 | 43045 | | ANDERSON | | |

PROVIDER NOS: BCBS9876 FA    FED-ID 41-9876543

STATEMENT CLOSING DATE 11/01/91

| | NEW CHARGES | TO PATIENT: FILE THIS COPY WITH YOUR INSURANCE COMPANY ONLY IF CHARGES ARE LISTED. |

XYZ PHYSICIANS, PA
RIDGE POINT MEDICAL BLDG
14050 NICOLLET AVE S SUIT
BURNSVILLE MN 55337

TO INSURANCE CO.: SEE REVERSE SIDE FOR CODING.
PLEASE EXPEDITE PAYMENT AS YOUR INSURED WILL CONTINUE TO RECEIVE
MONTHLY STATEMENTS UNITL ACCOUNT IS PAID IN FULL.

Fig. 16

```
10/05/91  09:56                    UNITED HEALTHCARE CORPORTATION                SITE MSP  PAGE   6
CONTROL NO. 91252 ─500       RELEVANT HISTORY FOR SELECTED REVIEW 35 CASES  510  UHC RPT NO. A14500-01
─────PENDING──────     ─502      ─504       ──HISTORY──  ─506
                                                           ─508            ─512      ─514
AUDIT-NUMBER  DT-RECVD   MEMBER-ID──     ──NAME──  D.O.S.  AUDIT NO(S)  PROVIDER  INIT  CROSS-REFERENCE
```

| AUDIT-NUMBER | | DT-RECVD | MEMBER-ID | | NAME | D.O.S. | AUDIT NO(S) | | PROVIDER | INIT | CROSS-REFERENCE |
|---|---|---|---|---|---|---|---|---|---|---|---|
| 04836082 | 00 | 09/13/91 | 70200 | 1234567 00 | SMITH, J | 10/15/91 | 04836081 | 00 | 12345 | KS | |
| | | | | | | | 04836083 | 00 | 98765 | | |
| | | | | | | | 04836084 | 00 | 1401496 | | |
| 04836083 | 00 | 09/13/91 | 70200 | | | 08/13/91 | 04836081 | 00 | 1401496 | KS | |
| | | | | | | | 04836082 | 00 | 1401496 | | |
| | | | | | | | 04836084 | 00 | 1401496 | | |
| 04836084 | 00 | 09/13/91 | 70200 | | | 08/13/91 | 04836081 | 00 | 1401496 | KS | |
| | | | | | | | 04836082 | 00 | 1401496 | | |
| | | | | | | | 04836083 | 00 | 1401496 | | |
| 26674472 | 00 | 09/13/91 | 61041 | | | 04/24/91 | 82848651 | 00 | 1708157 | | |
| 26674472 | 00 | 09/13/91 | 61041 | | | 04/26/91 | 82848651 | 00 | 1708157 | | |
| 26674472 | 00 | 09/13/91 | 61041 | | | 04/24/91 | 82955872 | 01 | 0417213 | | |
| 26674606 | 00 | 09/13/91 | 60060 | | | 04/05/91 | 26674608 | 00 | 0908020 | | |
| 26674632 | 00 | 09/13/91 | 46000 | | | 08/27/91 | 83314608 | 00 | 1708223 | | |
| 26676355 | 00 | 09/13/91 | 45006 | | | 06/22/91 | 26633169 | 00 | 0901984 | | |
| 26692884 | 01 | 09/13/91 | 32176 | | | 04/12/91 | 82902786 | 00 | 0701670 | | |
| 26692884 | 01 | 09/13/91 | 32176 | | | 04/17/91 | 82902786 | 00 | 0701670 | | |
| 26692884 | 01 | 09/13/91 | 32176 | | | 04/14/91 | 82902786 | 00 | 0701670 | | |
| 26692884 | 01 | 09/13/91 | 32176 | | | 04/22/91 | 82902786 | 00 | 0701670 | | |
| 26683440 | 00 | 09/16/91 | 59110 | | | 07/09/91 | 83094151 | 00 | 1916890 | | |
| 26683679 | 00 | 09/16/91 | 59130 | | | 06/19/91 | 26640257 | 00 | 0902655 | | |
| 26684209 | 01 | 09/16/91 | 59108 | | | 08/12/91 | 26684209 | 00 | 1320860 | AS | |
| 83335991 | 00 | 09/16/91 | 61464 | | | 09/10/91 | 83335995 | 00 | 1916838 | JO | |
| 83335995 | 00 | 09/16/91 | 61464 | | | 09/10/91 | 83335991 | 00 | 1916855 | JO | |
| 83336654 | 00 | 09/16/91 | 60060 | | | 01/08/91 | 14347783 | 00 | 1013934 | | |
| | | | | | | | 82447780 | 00 | 1016461 | | |
| | | | | | | | 83259010 | 00 | 1016461 | | |
| 26686168 | 00 | 09/17/91 | 45031 | | | 03/22/91 | 82780509 | 00 A | 0114223 | | |
| | | | | | | | 82780509 | 00 | 0114223 | | |
| | | | | | | | 83219205 | 00 | 0114223 | | |
| 83343959 | 00 | 09/17/91 | 59200 | | | 06/21/91 | 26679912 | 00 | 0704399 | BT | HIST, OB |
| | | | | | | | 83064397 | 00 A | 0704399 | | |
| | | | | | | | 83064397 | 00 | 0704399 | | |
| | | | | | | | 83237831 | 00 | 0704399 | | |
| 83345218 | 00 | 09/17/91 | 70205 | | | 09/10/91 | 83348213 | 00 | 0121389 | KS | |
| 26686976 | 00 | 09/18/91 | 70200 | | | 07/22/91 | 26686974 | 00 | 1722057 | | HIST, OTHER |
| 26687223 | 00 | 09/18/91 | 61025 | | | 09/03/91 | 04839814 | 00 | 0701806 | | |
| 26687353 | 00 | 09/18/91 | 60790 | | | 08/08/91 | 04797643 | 00 | 0702970 | | |

Fig. 17

CLAIM REPORT

10/21/91 11:26  
CONTROL NO: 91302 — 500  
-------PENDING--------  
AUDIT-NUMBER  DT-RECVD  MEMBER-ID  -----NAME-----  -D.O.S.-  INIT PROCEDURE  CLAIMED  ELIGIBLE  RSN  NEW ELIG  RSN  
                502            504                506        518  516      520      522      524       526       528  
                                                                              ----REASON----  254

SITE PVD PAGE 2  
UHC RPT NO. A14600-00

| AUDIT-NUMBER | DT-RECVD | MEMBER-ID | NAME | D.O.S. | INIT PROCEDURE | | CLAIMED | ELIGIBLE | RSN | NEW ELIG | RSN |
|---|---|---|---|---|---|---|---|---|---|---|---|
| 20204213 00 | 08/14/91 | 21099 035527462 00 | UNKNOWN NAME | 05/10/91 | BILAT | | | | | | |
| | | | | | 12345 | 97 | 125.77 | 125.00 | 30 | 120.00 | 35 |
| | | | | | 55545 | 97 | 225.77 | 225.00 | 30 | 220.00 | 35 |
| 20204213 00 | 08/14/91 | 22099 035527462 00 | UNKNOWN NAME | 05/10/91 | BILAT | | | | | | |
| | | | | | 12345 | 97 | 1125.77 | 1125.00 | 30 | 1120.00 | 35 |
| | | | | | 55545 | 97 | 1225.77 | 1225.00 | 30 | 1220.00 | 35 |
| 20204213 00 | 08/14/91 | 23099 035527462 00 | UNKNOWN NAME | 05/17/91 | ILN-UD | | | | | | |
| | | | | | 12345 | 97 | 2125.77 | 2125.00 | 30 | 2120.00 | 35 |
| | | | | | 55545 | 97 | 2225.77 | 2225.00 | 30 | 2220.00 | 35 |
| 20204213 00 | 08/14/91 | 24099 035627462 00 | UNKNOWN NAME | 05/17/91 | TONSIL | | | | | | |
| | | | | | 12345 | 97 | 3125.77 | 3125.00 | 30 | 3120.00 | 35 |
| | | | | | 55545 | 97 | 3225.77 | 3225.00 | 30 | 3220.00 | 35 |

HEALTH CARE PAYMENT ADJUDICATION AND REVIEW SYSTEM

TECHNICAL FIELD

The present invention relates to a method and apparatus for processing medical health care payment requests received by a health care insurer or payment processor from a health care provider. In particular, the present invention pertains to a method and apparatus for analyzing health care payment requests to determine whether or not to honor the request and the amount of payment if the request is honored.

BACKGROUND ART

The costs of health care today are rapidly increasing as the health care industry becomes more complex, specialized and sophisticated. Health care costs have more than doubled during the past decade, rising to $676 billion today. The federal government predicts health care cost increases of 12–15 percent each year for the next five years.

Over the years, the delivery of health care services has shifted from local physicians to large managed health care organizations. This shift reflects the growing number of medical, dental and pharmaceutical specialists and the complexity and variety of health care options and programs. This complexity and specialization has created large administrative systems that coordinate the delivery of health care between health care providers, administrators, patients, payers and insurers. The cost of supporting these administrative systems has been steadily rising, contributing to today's rising costs of health care.

One area for lowering administrative costs is the review and adjudication of health care provider payment requests. Such payment requests typically include bills for procedures performed and supplies given to patients. Careful review of payment requests minimizes fraud and unintentional errors and provides consistency of payment for the same treatment.

Unfortunately, present decision techniques for adjudicating payment requests are manual-based systems which are complex, labor intensive and time consuming. The number of payment requests can be staggering. For example, a large health care management organization may review more than 75,000 requests each day or 25 million payment requests each year. Because of the overwhelming administrative costs of an in-depth review of each of these requests, a majority of these requests are simply paid without extensive review.

Present manual decision techniques for performing an in-depth review of payment requests requires trained health care professionals, known as medical analysts, who are familiar with terminology and practices of the medical profession. Often medical analysts have been trained as registered nurses or surgical technicians with a medical surgical background. In addition to their medical training, medical analysts may receive up to one year of additional training in how to review payment requests before they are able to analyze payment requests properly.

To manually review a payment request, the medical analyst begins by categorizing the payment request according to the priority of the type of review required. The type of review varies depending on the procedures and supplies to be reviewed for payment.

The medical analyst then examines the payment request to see that the procedures for which payment is requested are valid and consistent with current medical procedures. A primary reference for medical analysts is a volume titled Physicians' Current Procedural Terminology (CPT) which is maintained and updated annually by the American Medical Association. This book contains a listing of descriptive terms and numeric identifying codes and code modifiers for reporting medical services and procedures performed by physicians. Thus, the CPT describes procedures and services consistent with current medical practice and lists a corresponding procedure code that is stated on a payment request.

Next, the medical analyst reviews the history of prior payment requests for the patient to ensure that the current payment request is consistent with the historical requests and to determine if the historical requests will affect payment of the current request. Earlier requests may affect payment of the current payment request depending on the contractual arrangements among the provider, patient and payer. For situations where more than one surgical procedure is performed on the same day, about two thirds of the payment requests reviewed by medical analysts typically require review of historical payment requests. During adjudication, each historical payment request is examined manually. This is very time consuming because frequently prior payment requests do not have any effect on the current request the analyst is examining, yet the analyst must look at them.

After examining the historical payment requests, the medical analyst next compares the payment request with the contractual obligations of the payer to determine whether or not to pay the request and if payment is to be made, what amount to pay. These contractual obligations change frequently and involve complex relationships between payers and health care providers. The amount of payment will vary by the service or procedure, by the particular contractual arrangements with each provider or physician, by the contractual arrangements between the payer and the patient regarding who pays for what procedures and treatments to what extent, and by what is considered consistent for this procedure under current medical practice.

One example of a special contractual relationship between a payer and a health care provider occurs, on occasion, when a payer offers a physician more than the standard fee. This may occur when the physician is in a rural or remote area and practices a particular medical specialty or performs particular procedures, and, by paying a higher than usual fee, the payer hopes to encourage the physician to remain in the rural area and to continue to provide the specialized services to people in the area.

An example of the complex contractual relationship between payer and health care provider occurs when a provider performs more than one surgical procedure on the same patient in the same day. The amount of payment depends on several factors, such as, for example, whether the operation was performed through one incision or two incisions or through a physical opening such as an ear or nose, whether the contractual arrangements distinguish between bilateral procedures, requiring two incisions for performing the procedure on each side of the body, and non-bilateral procedures, whether the position and number of incisions are consistent with current medical practice for performing the procedure, whether other procedures followed by the physician are consistent with current medical practice, how much the physician has requested as payment for each procedure and whether the physician receives more or less than the standard fee for performing this procedure.

For example, a physician specializing in ear, nose and throat, may perform a procedure called a tympanostomy, which involves inserting a ventilating tube in a child's ear to minimize ear infections. The amount of payment to the physician for a tympanostomy depends on several factors, including: whether the operation was performed through one or more incisions, whether the position and number of incisions made are consistent with current medical practice for performing a tympanostomy, whether payer/provider contractual arrangements distinguish between placing tubes in both ears at the same time and placing a tube in each ear in separate operations on separate days, whether any other procedures followed by the physician are consistent with current medical practice for performing a tympanostomy and whether the physician has requested the full amount payable by the payer for performing a tympanostomy.

The medical analyst relies on several sources of information to make these decisions such as the CPT and manuals detailing contractual relationships among payers, providers and patients. Many of these sources are dynamic, changing frequently to reflect new medical procedures and cost structures. Presently, medical analysts stay current with new medical practices and payer payment obligations via notices and announcements made at periodic medical analyst meetings. The typical medical analyst records these changes in meeting notes or relatively unorganized pencilled notes in the reference volumes. With so much complex interrelated information changing constantly, it is difficult for medical analysts to keep their knowledge up-to-date.

The increased workload can become overwhelming to current medical analyst staffs, sometimes causing inconsistent and shallow payment reviews, resulting in further review cycles and possibly legal ramifications. Increasing medical analysis staff is a costly measure and not necessarily an efficient or effective solution.

Though it would be possible to organize the medical analyst's resources in a more organized, accessible form electronically, conventional programming methods do not allow for such complex, integrated information to be changed frequently, updated quickly and melded easily with historical payment requests in order to review and adjudicate payment requests quickly and accurately without extensive human intervention.

An example of using conventional programming methods to computerize the adjudication of payment requests is the Gabriel Management Information System (GMIS) marketed by GMIS of Philadelphia, Pa. The GMIS system includes a large database of relatively fixed, permanent tables that contain the payment patterns for different combinations of procedure codes. Storage of such a large database typically requires the resources of a computer mainframe system. As those skilled in the art will appreciate, accessing data contained in such a large database on a mainframe is processor intensive. Maintenance of such a large database is staggering because the database is so unwieldly. It generally takes about six months to update the database with the annual changes in the CPT manual alone. In addition, a large database created using conventional computer techniques such as the GMIS system is not flexible enough to vary the payment patterns based on information contained in historical payment requests. Consideration of historical payment requests is critical to adjudicating a payment request completely and accurately.

A method and apparatus that minimizes the use of expensive mainframe resources and is capable of storing and organizing the great amount and complexity of information required to adjudicate payment requests in a form that is readily accessible despite frequent changes and updates, of pre-screening historical payment requests to determine which requests are relevant for a particular review, of analysing and making payment decisions based on relevant historical payment requests, current medical practices and contractual arrangements between payer and provider or between payer and patient would be a great benefit. The creation of such a method and apparatus would increase medical analyst productivity, provide consistent payment of payment requests and help lower the costs of health care.

SUMMARY OF THE INVENTION

The problems described above are in large measure solved by the medical health care payment request adjudication method and apparatus in accordance with the present invention. In particular, the method and apparatus in accordance with the present invention uses pre-determined review criteria to screen historical payment requests for historical payment requests relevant to the review of the current payment request; defines a master list of payable payment requests given current medical procedures, the pre-determined parameters of the review and the contractual arrangements between the payer, patient and health care provider; codifies a set of interpretive rules for analysis of the payment requests based on the pre-determined parameters of the review, the contractual arrangements between the payer, patient and health care provider and current medical procedures; analyses the current payment request according to the relevant historical payment requests and the master payable list by applying the interpretive rules to this information; and develops and reports payment decisions based on that analysis.

BRIEF DESCRIPTION OF THE DRAWINGS

FIGS. 2a and 2b are examples of payment requests for the same patient from different health care providers;

FIG. 17 is an example of a report listing payment decisions and recommended courses of action provided to medical analysts.

DETAILED DESCRIPTION OF THE DRAWINGS

Figure 1:
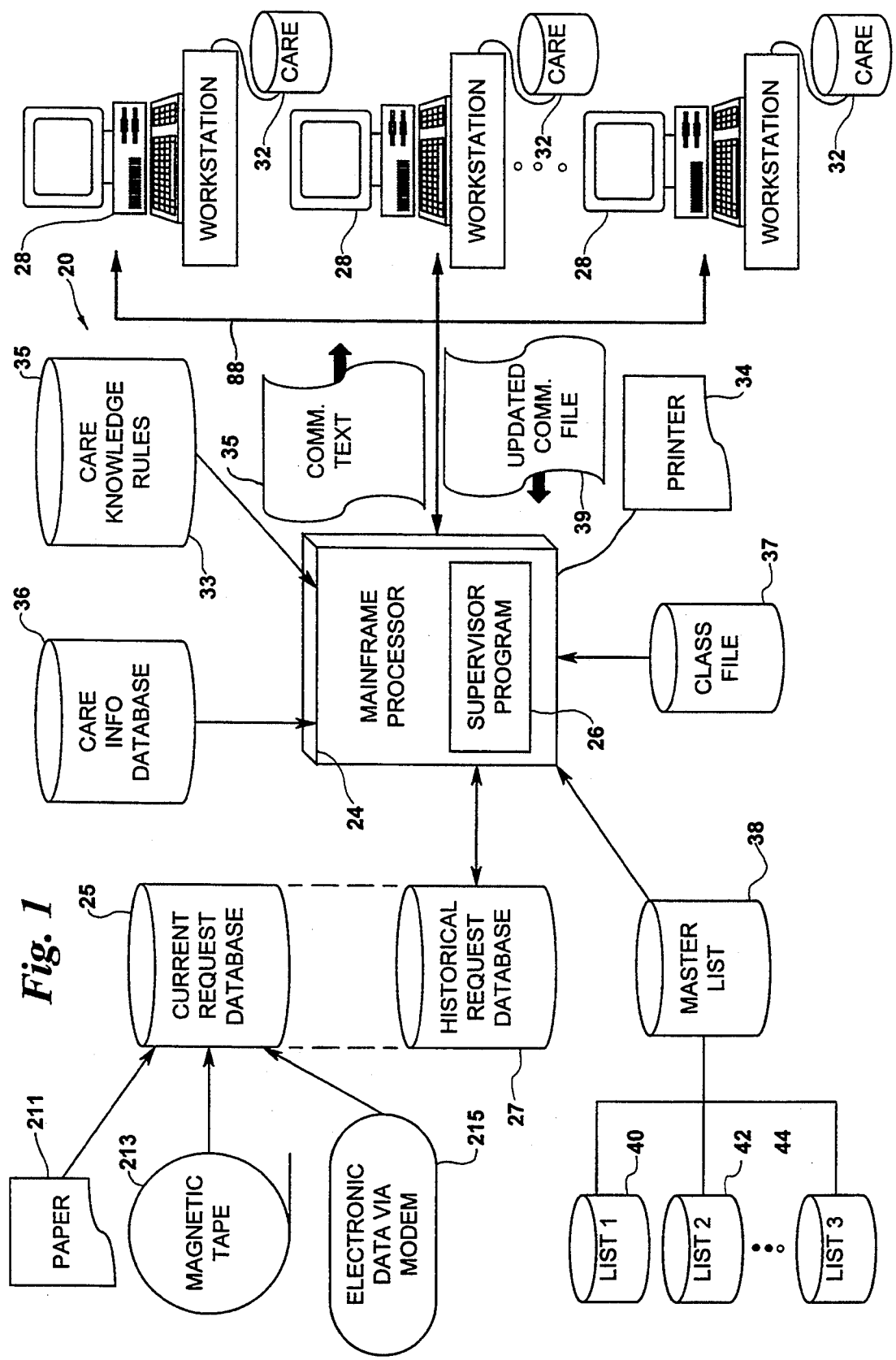
FIG. 1 is a schematic view of a system in accordance with the present invention.

Referring to the drawings, a system 20 for adjudicating health care payment requests broadly includes a network of computer processors 22, a current payment request database 25, a historical payment request database 27, a masterlist database 38, a number of stored lists of information 40, 42, 44, a class file database 37, a plurality of workstations 28 and a printer 34.

The network of computer processors 22 broadly includes a mainframe computer processor 24 and a plurality of minicomputer or microcomputer workstations 28. Each computer processor 24, 28 broadly includes memory and storage containing the information organized by and included in an expert system 32 and an expert system information database 36. As those skilled in the art will understand, the expert system 32 is a rule-based knowledge engineering system. The expert system 32 broadly includes a supervisor program 26 and an expert system knowledgebase 33 embodying user specific requirements for accomplishing the task of adjudicating health care payment requests. The expert system knowledgebase 33, broadly defined, is the repository of the rules and applies the rules to the payment request data. Those skilled in the art will understand that for ease of maintenance, the expert system 32 comprised of the expert system knowledgebase 33 and supervisor program 26 resides on the mainframe processor 24 and is distributed to individual workstations 28 for operation. (References throughout the specification to expert system 32 refer to CARE 32 in the drawings. References throughout the specification to expert system information database 36 refer to CARE Info Database 36 in the drawings. References throughout the specification to expert system knowledgebase 33 refer to CARE Knowledgebase 33 in the drawings.)

The payment request database 25 broadly includes storage for payment request information received on paper 211, or on magnetic tape 213 or from a remote computer 28 via communications equipment 215. The historical payment request database 27 broadly includes storage for payment request information that has already been received. As those skilled in the art will understand, the payment request database 25 and the historical request database 27 are functionally the same database storing all payment request information currently received or received earlier, and will be referred to hereinafter by the single reference number 25.

As those skilled in the art will appreciate, the computer processor 22 may be a mainframe computer or a powerful microcomputer or any combination of the computer processors in a multiprocessor network, such as, for example, an Unisys A Series mainframe computer and Toshiba model T5200 workstation running the MS DOS operating system. Those skilled in the art will also understand that a variety of expert system shells, such as, for example, Unisys' Knowledge Engineering System II (KES II) expert system shell, and programming languages, such as, for example, COBOL, ALGOL or C programming languages or a combination thereof, comprise the expert system 32.

The format of payment requests received for input to the system 20 may vary widely, depending on the insurer's style and need. Referring to FIG. 2a & 2b, a paper payment request 46, 48 broadly includes patient identification information 50, health plan identification information 52, health care provider name and address 54, insured's name and address 56, a listing of procedures and supplies provided to the patient 58 and the payment request date 76, 80. The listing of procedures and supplies broadly includes separate lines for each procedure or supply 60, 62, 64, 66, 78. Each line broadly includes the date of the service 68, the patient name and explanation of the service 70, the CPT code corresponding to the procedure performed 72 and the performing physician's name 74. The information for each line 60, 62, 64, 66 and 78, is organized in pre-determined fields that define an individual payment request and are entered and stored in electronic form in the payment request database 25.

Figure 3:
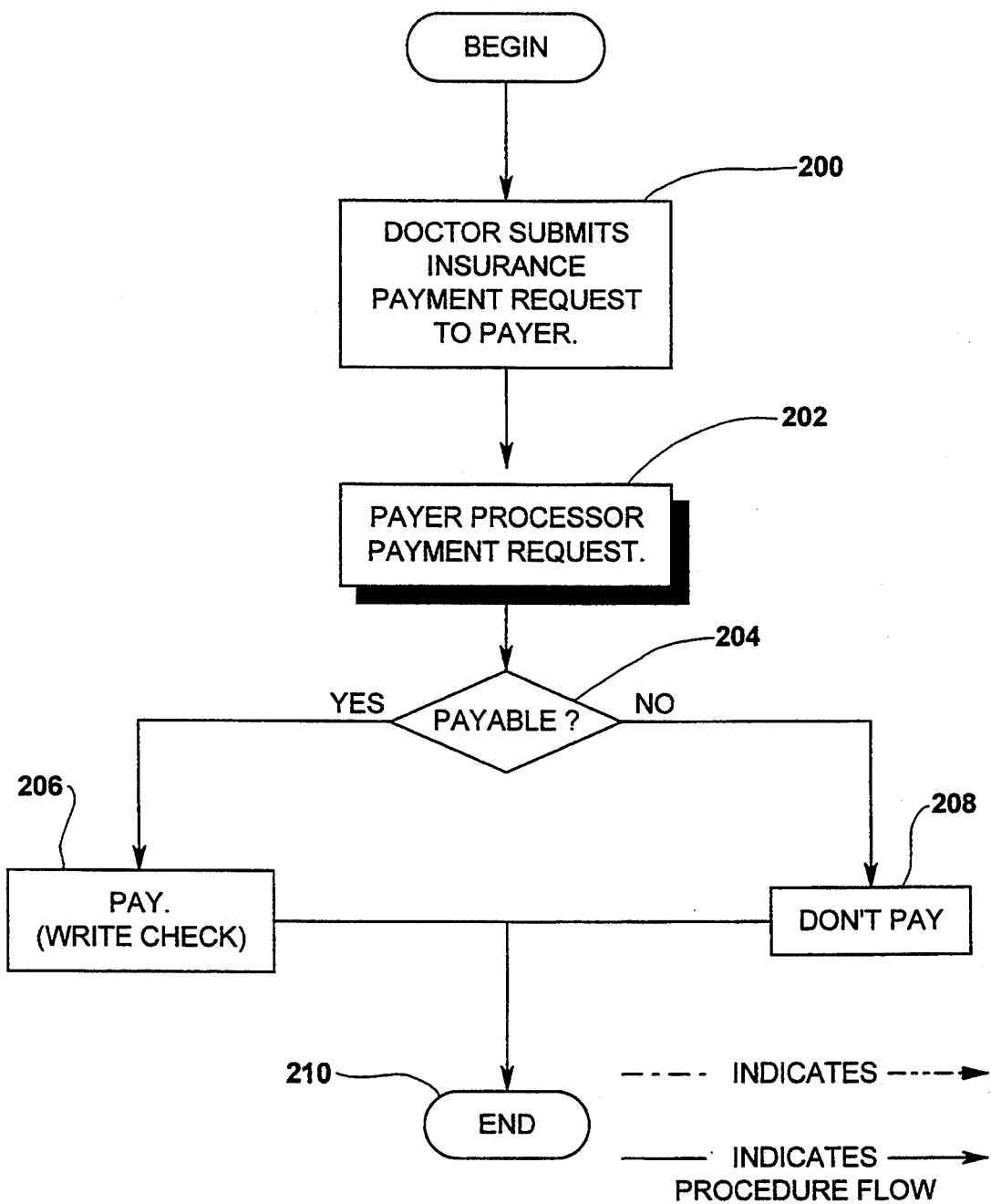
FIG. 3 is a logical flow diagram depicting the overall operation of the present invention.

Referring to FIG. 3, the broad steps of processing a health care claim are depicted in flow chart form. The process begins with the health care provider, typically a physician, submitting a payment request to payer for services and materials provided to a patient (step 200). Typically, the payer is an insurer that offers a health insurance plan that may or may not require the patient to pay part of the costs for the services and materials provided.

Next, the payer processes the payment request (step 202) to determine whether to pay the request and if so, whether to pay all or only part of the payment request. Once the payer makes its payment decision (step 204), the payer writes a check (step 206) or doesn't write a check (step 208) to the health care provider and the system ends (step 210).

Figure 4:
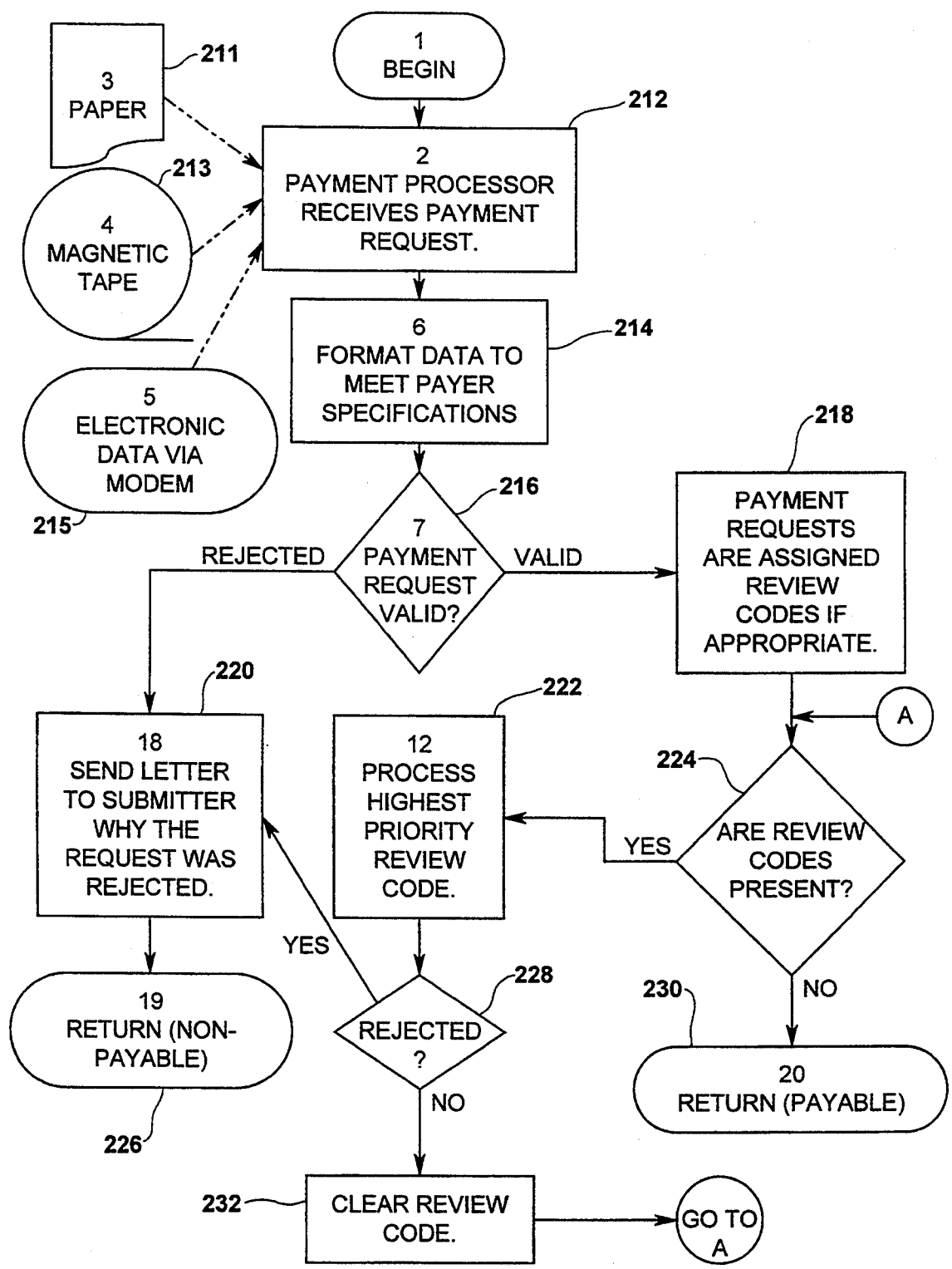
FIG. 4 is a flow chart depicting in greater detail the payer processes payment request step of FIG. 3.

The health care payment adjudication and review system 20 is employed in conjunction with the payer processes payment request step 202 of FIG. 3 which is set out in greater detail in FIG. 4. The payer processes payment request step 202 begins with the payment processor receiving and storing the payment request (step 212). The payment processor may be the payer or insurer itself or an organization that payer or insurer has contracted with to process health care payment requests. The payment processor may receive the health care payment request from the health care provider in one of three forms: on paper 211, on magnetic tape 213 or as electronic data through a network 215. The payment processor will store the payment request in the payment request database 25.

Next, the processor organizes the payment request data in the order and manner necessary to meet payer specifications (step 214). The system 20 then tests whether the payment request is valid (step 216), meaning the system tests whether the payment request contains all the information pre-determined by the user of the system as necessary for entry into the system 20 to process the request. For example, the system 20, at a minimum, should determine whether the health care provider submitting the payment request is participating in a plan covered by the payer and whether the patient is covered by the insurance plan of the payer. Other entry requirements could be set. If the request does not contain all the information predetermined to be necessary for entry into the system, the system 20 rejects the request and alerts the submitter of the request that the request was rejected (step 220). The system 20 then returns and the payment request is processed as a nonpayable request (step 226).

If the payment request includes all the necessary information, the system 20 assigns review codes to listed procedures based on the procedure codes from the CPT (step 218). A review code for multiple surgical procedures, for example, could be assigned to each surgical procedure on a payment request having more than one surgical procedure listed for the same day for the same patient. A second review code could be assigned to CPT procedure codes indicating participation of an assisting surgeon. The review codes can be used to determine whether the payment request will receive further review or will be paid without further review. Because certain classes of procedures rarely present issues of fraud or overpayment when presented for payment, such procedures bearing a recognized review code can be automatically eliminated from the review process.

Next, the system 20 determines whether review codes requiring further review are present on any line in the payment request (step 224). If no such review codes are present, the system 20 assumes that the entire payment request is payable and returns (step 230). If review codes requiring further review are present, the system 20 processes the line item with the highest priority review code (step 222). The priority of review codes is pre-determined by the user of the system 20 following the perceived likelihood of fraud or mistake for that type of procedure or payment request. For example, a review code indicating a review for the presence of an assisting surgeon could be considered a higher priority than a review code indicating review of more than one surgical procedure performed on the same day for the same patient, and would be processed first.

Those skilled in the art will understand that the examples provided herein are merely illustrative of the great number and combination of health care services, procedures and materials for which payment may be requested, of current medical practices and of possible contractual obligations between payers, health care providers and patients. Each user of the system 20 will have its own particular review criteria based on contractual obligations, patient and provider payment request patterns, and the like. The examples given herein will be recognized as typical to those encountered within the art.

After the system 20 processes the highest priority review code listed on the payment request (step 222), the system 20 tests the results of the review to determine whether the review process rejected the payment request or not (step 228). As those skilled in the art will appreciate, the payment requests may be rejected during the review process for a variety of reasons, such as, for instance, the payment requests fail to conform with current medical practice. For example, a payment request asking for payment for a hysterectomy performed on a male patient would be rejected because the procedure is inconsistent with the patient's gender.

If the review process rejected the payment request, the system 20 rejects the request and alerts the submitter of the request that the request was rejected (step 228). The system 20 then returns and the payment request is processed as a nonpayable request (step 226).

If the system 20 does not reject the payment request, the system 20 eliminates or clears the review code from that line on the payment request (step 232) and then repeats steps 224 through 232, as needed, until there are no review codes assigned to any lines on the payment request.

It will be appreciated that, when the individual line items 60, 62, 64, 66, 78 in a payment request require different types of reviews, the payment request as a whole will be reviewed during each type of review. For example, the first line item 60 and the third line item 64 in FIG. 2a include procedures that were performed on the patient on the same day and so a user might designate the appropriate review type as a multiple surgical review. The fourth line item 66 in FIG. 2a includes a procedure code that indicates that the provider assisted in performing the procedure. In this example, a user might designate the appropriate review type as those adjudicating payment requests where providers assisted in performing the procedures. Thus, for the payment request described in FIG. 2a, two different types of reviews could be performed, depending upon the user specific review criteria.

Figure 5:
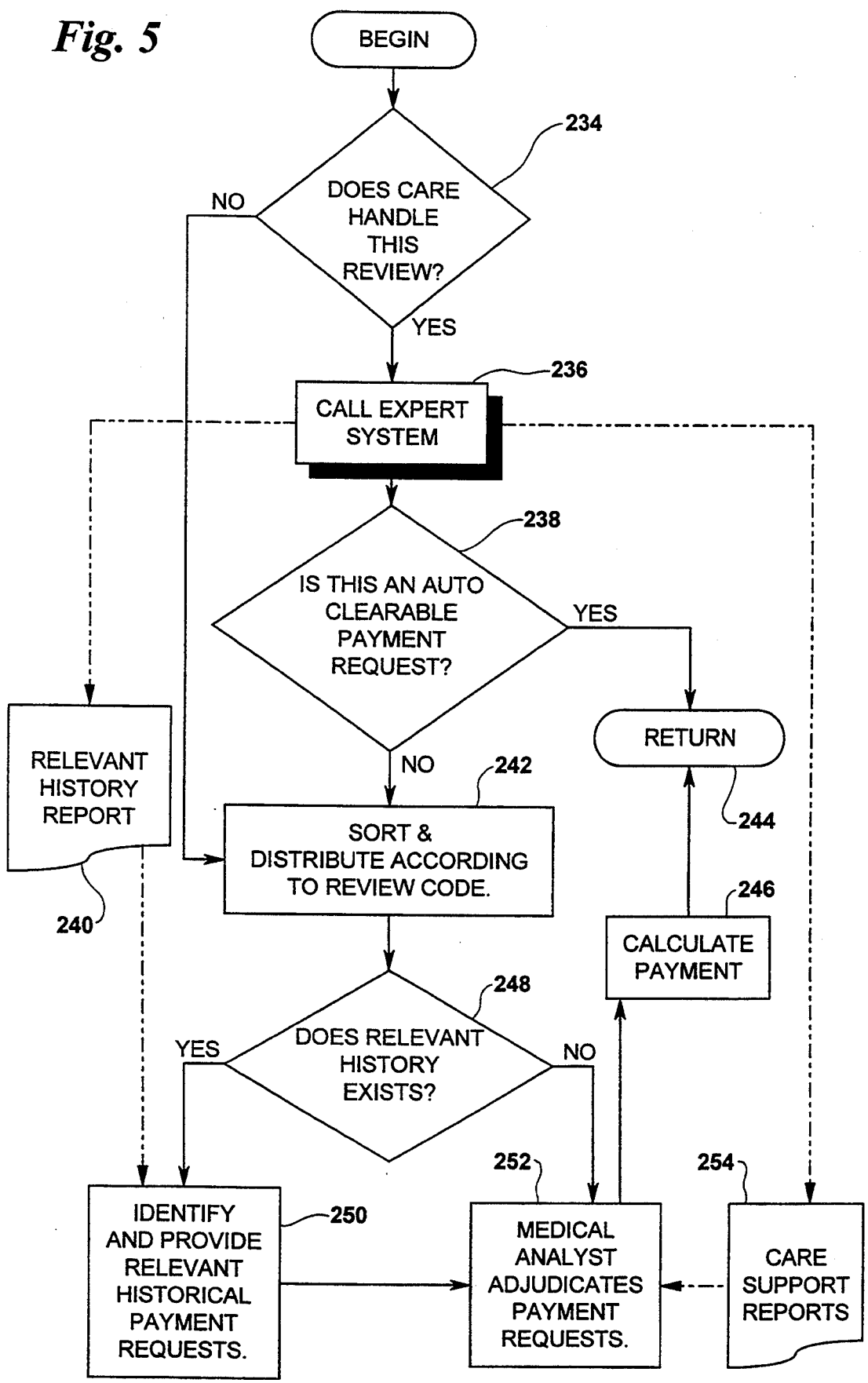
FIG. 5 is a flow chart depicting in greater detail the process highest priority review code step of FIG. 4.

FIG. 5 depicts in greater detail the process highest priority review code step 222 of FIG. 4. The process highest priority review code step 222 of FIG. 4 begins by testing whether the expert system is configured to process the particular review code under consideration (step 234). The configuration of the expert system will be individualized for particular users based on contractual and other criteria of the system user in the payment of payment requests. If the expert system 32 is configured to process the review code, the system 20 accesses the expert system 32 (step 236). Once the expert system 32 has processed the payment request, the system 20 tests whether the expert system 32 has determined if the payment request is auto-clearable (step 238). A payment request is auto-clearable if the payment request requires no further review and adjudication and can automatically be accepted, denied or rejected. The determination of what types of payment requests are auto-clearable is determined by the users of the system 20 according to the likelihood of fraud or a mistake in the payment request. If the expert system 32 indicates that the payment request is auto-clearable, the system 20 returns (step 244).

In particular, for example, when reviewing a payment request where more than one surgical procedure occurred on the same day, if the expert system 32 discovers that the payment request contains only a single line for this procedure indicating the procedures were performed at a surgi-center ( a facility specifically designed to economize surgical costs) and there are no relevant historical payment requests, the expert system 32 could indicate that the request is auto-clearable and so needs no further review before payment.

If the expert system 32 indicates that the payment request is not auto-clearable and so requires further review, the system 20 sorts the payment requests according to the review codes (step 242) for distribution to the medical analysts. Since the medical analysts frequently specialize in the type of payment requests they review, sorting the payment requests by review code ensures that each analyst receives the type of payment requests they specialize in reviewing.

After sorting the payment requests by review code, the system 20 tests whether there are any relevant historical payment requests that are required by the medical analysts to review the payment request (step 248). If there are relevant historical payment requests, the system 20 identifies which historical payment requests are relevant (step 250). The system 20 obtains historical payment requests from the historical payment request database 27 which contains an archive of all payment requests for an individual since the date of coverage on the particular health care plan (step 250).

The system 20 then provides the medical analysts with payment request 240 information, any relevant historical payment requests and any expert system supporting reports 254 that may be available to assist the medical analysts in reviewing and adjudicating the payment request (step 252). The expert system supporting reports 254 include, for example, cross references from one type of review to other reviews for the same payment request, notice of which analyst is handling which reviews, the current status of the review and recommended adjudication and payment decisions. This information may be provided to medical analysts in the form of a paper report or displayed interactively on a display screen. Once the medical analysts have received this information, the system 20 returns (step 244) after calculating the payment (step 246).

One type of payment request for which a system user might require further review by medical analysts could occur, for example, when the review code indicates a payment request involving more than one surgical procedure performed on the same day and there are no relevant historical payment requests and the surgery was not performed at a surgi-center. Because of the high possibility of mistake or incidence of fraud and the difficulty in identifying the reason for the absence of historical payment request information, users of the system 20 would designate this type of payment request as requiring further review by a medical analyst.

Figure 6:
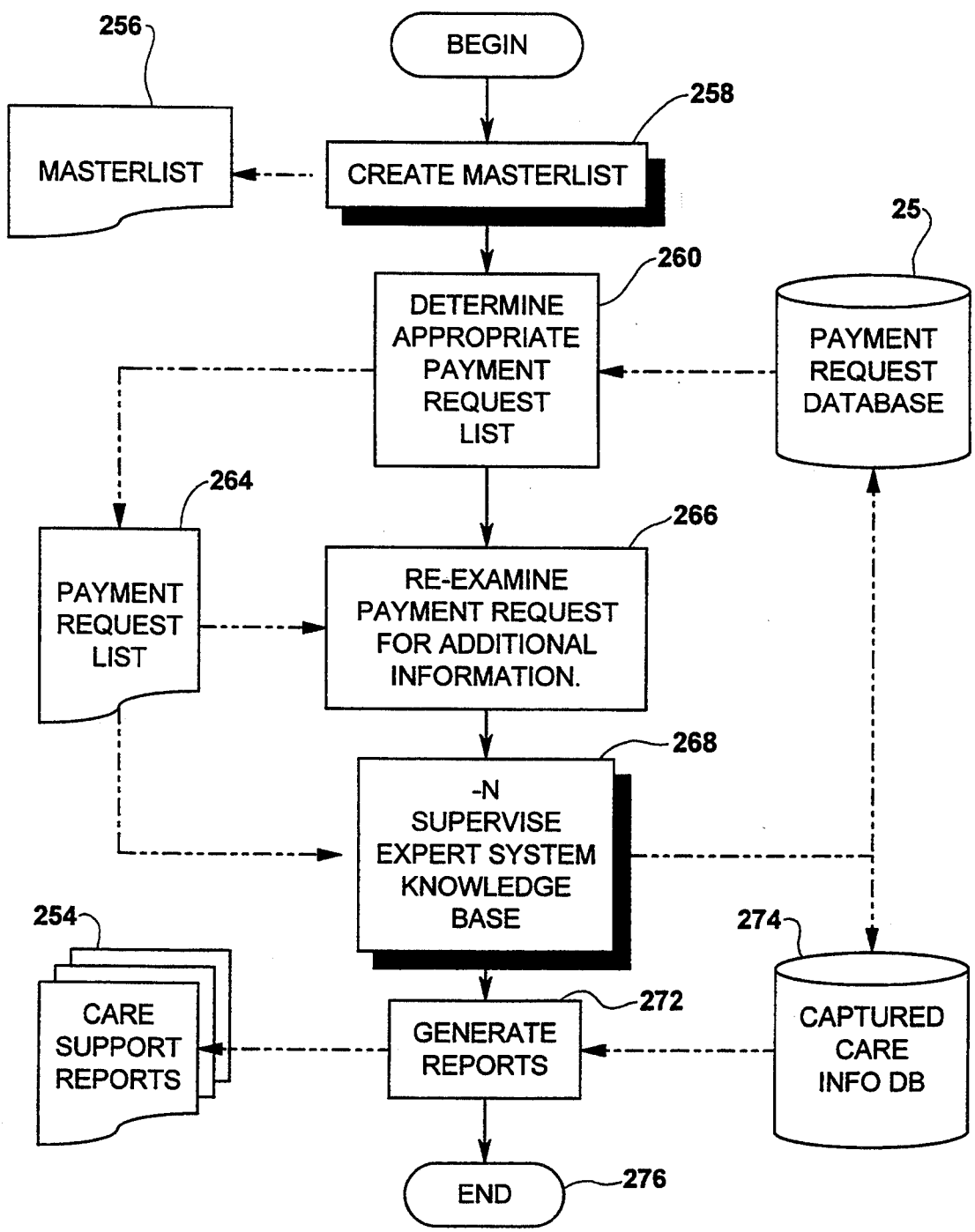
FIG. 6 is a flow chart depicting in greater detail the call expert system 32 step of FIG. 5.

FIG. 6 depicts the call expert system 32 step 236 of FIG. 5 in greater detail. The call expert system 32 step 236 begins by creating a Masterlist 256 (step 258). The Masterlist broadly defined is a composite list of procedures from the CPT identified with various numerical attributes which correspond to pre-defined characteristics of each procedure. These characteristics are pre-defined by the user as useful for reviewing and adjudicating payment requests in accordance with the user's own predetermined review criteria. An example of the characteristics that could be included in creating a Masterlist is provided below in conjunction with the description of FIG. 7.

Once called, the expert system 32 creates an appropriate payment request list (step 260) by collecting all the payment requests that have the same review codes and are currently awaiting review. The resulting payment request list 264 is then reexamined to ensure that all the payment requests have been located (step 266). The user determines which situations require reexamination. For example, reexamination could be performed when a second surgeon assists on an operation because the second surgeon's payment request should be considered at the same time as the primary physician's request despite any time lag in the payer or payment processor's receipt of either surgeon's payment request.

Next, the system 20 begins the supervise expert system knowledgebase step 268. The expert system knowledgebase 33 contains rules which embody relationships between the procedure attributes of the Masterlist 256 and user defined desired outcomes made as the expert system knowledgebase 33 reviews each payment request. The supervise expert system knowledgebase step 268 is defined in greater detail below in conjunction with the description of FIG. 8.

Once the system 20 completes the supervise expert system knowledgebase (step 268), the system 20 uses the information obtained from the expert system knowledgebase 33 during adjudication and stored in the expert system information database 274 to generate any expert system supporting reports 254 (step 272). Examples of such expert system supporting reports include the relevant historical payment request report described above and the clear payment request report depicted in FIG. 17 below. After generating the expert system supporting reports 254, the system 20 then returns (step 276).

Figure 7:
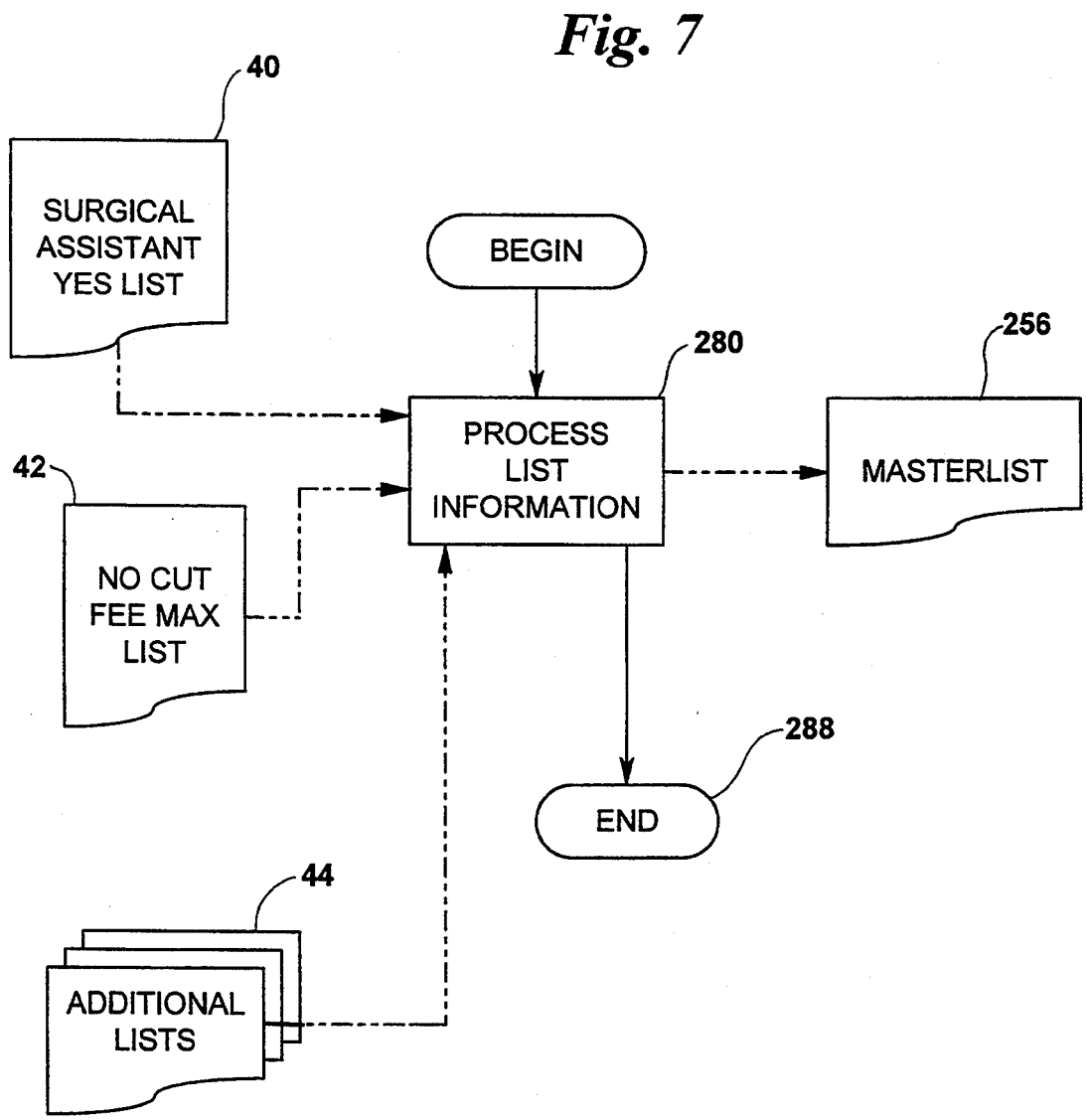
FIG. 7 is a flow chart depicting in greater detail the create Masterlist step of FIG. 6.

FIG. 7 depicts the create Masterlist step 258 of FIG. 6 in greater detail. The information contained in the Masterlist 256 is specific to the type of review being performed, and is created from the lists 40, 42, 44 each time the step 258 is performed such that the Masterlist 256 is continuously updated. As described in detail below, the lists 40, 42, 44 are collections of CPT procedures organized according to user defined characteristics, such as all procedures involving bilateral surgical operations, or all procedures for which full payment of a claim is always made. Other types of lists could include listings of base codes as listed in the CPT, listings of mutually exclusive or inclusive CPT base codes, listings of CPT procedure codes which always require a review of relevant historical payment requests, listings of CPT procedures where payment for an assisting surgeon is allowed, listings of procedures that are specially designated within the CPT, listings of procedures not specifically listed in the CPT, and listings of procedures that would logically fall within a specific review code.

The Masterlist 256, when made up from selected ones of the lists 40, 42, 44, would broadly include, at a minimum, a list of CPT procedure codes, ordered numerically from low to high, each procedure's user defined characteristic as detailed above and indicated by the individual lists 40, 42, 44 that included that procedure, and a corresponding value for the user defined characteristic based on information contained in each individual list 40, 42, 44. The corresponding values are determined by the system user in the context of current, locally accepted medical practices as embodied in the CPT and specific contractual arrangements between the payer and patient which affect the decision of whether to honor the payment request and, if honored, to what dollar amount.

For example, a procedure appearing in an individual list which contains all procedures for which full payment of a claim is always made could be listed on the Masterlist 256 with the characteristic of always receiving full payment with a value indicating the reason that this procedure always receives full payment. Continuing this example, the user defined range of values describing reasons for making full payment for these procedures could include the fact that the procedure involves an excision, debridement, injection, repair, puncture or a diagnostic or adjunct procedure or a combination of these. An example from a sample masterlist incorporating the above characteristics and values for several CPT procedure codes is provided in Appendix A.

For another example, a procedure appearing on an individual list which contains all procedures involving bilateral surgical operations could be listed on the Masterlist 256 with the characteristic of being a bilateral procedure and with a value indicating a payment multiplier to be considered when calculating any payment for this procedure. Continuing this example, the range of possible values for the payment multiplier would depend on the specific contracutal arrangements between the payer and the physician.

Each Masterlist 256 for a particular review is created by combining a predefined user specific set of individual lists 40, 42, 44 (step 280) and then returns (step 288). For example, in creating the Masterlist 256 for review of payment requests involving multiple surgical procedures performed on the same person on the same day, the Masterlist 256 could include, among other individual lists, a list of procedures in which the characteristic indicates that full payment is always made for this procedure and a list of procedures in which the characteristic indicates that the payer will pay for another surgeon to assist in that procedure.

The Masterlist 256 provides information to the expert system knowledgebase 33 in the course of the knowledgebase's 33 review of payment requests and making payment decisions. It will be understood that the specific rules in the knowledgebase 33 are user specific based on individual contractual relations between a payer and provider or between a payer and patient. For example, the knowledgebase 33 may contain a rule that states that some procedures not listed in the CPT are not payable under the system user's contractual arrangements. Continuing this example, the knowledgebase 33 will examine the Masterlist 256 to see if the particular procedure for which payment is requested has a characteristic indicating it is an unlisted procedure. As those skilled in the art will appreciate, a Masterlist 256, when used in combination with the rules of the knowledgebase 33, provides the means for the automatic adjudication of health care payment requests without the cumbersome one-to-one correlation of request to payment criteria required by prior art systems.

As those skilled in the art will appreciate, the creation of a Masterlist 256 maximizes processing efficiencies by providing all list information in a standard organized form in a single source. A single Masterlist 256 for each type of review is capable of representing complex multifaceted relationships among numerous charateristics for each procedure with differing values in the context of frequently changing CPT procedure codes, historical payment request information and user specific contractual arrangements among payers, providers and patients. As those skilled in the art will understand, a simple table requiring a one-to-one or two-to-one correlation between payment decisions, CPT procedure codes and perhaps one characteristic of a procedure would not provide sufficient information to make payment decisions that closely tailor 'the amount paid with the procedure performed. The high level of precision in tailoring the amount of payment to the procedure performed in the context of historical payment requests, current medical practices and payer-physician contractual arrangements afforded by the system 20 results in an overall reduction in the cost of health care as health care dollars are more efficiently allocated.

Figure 8:
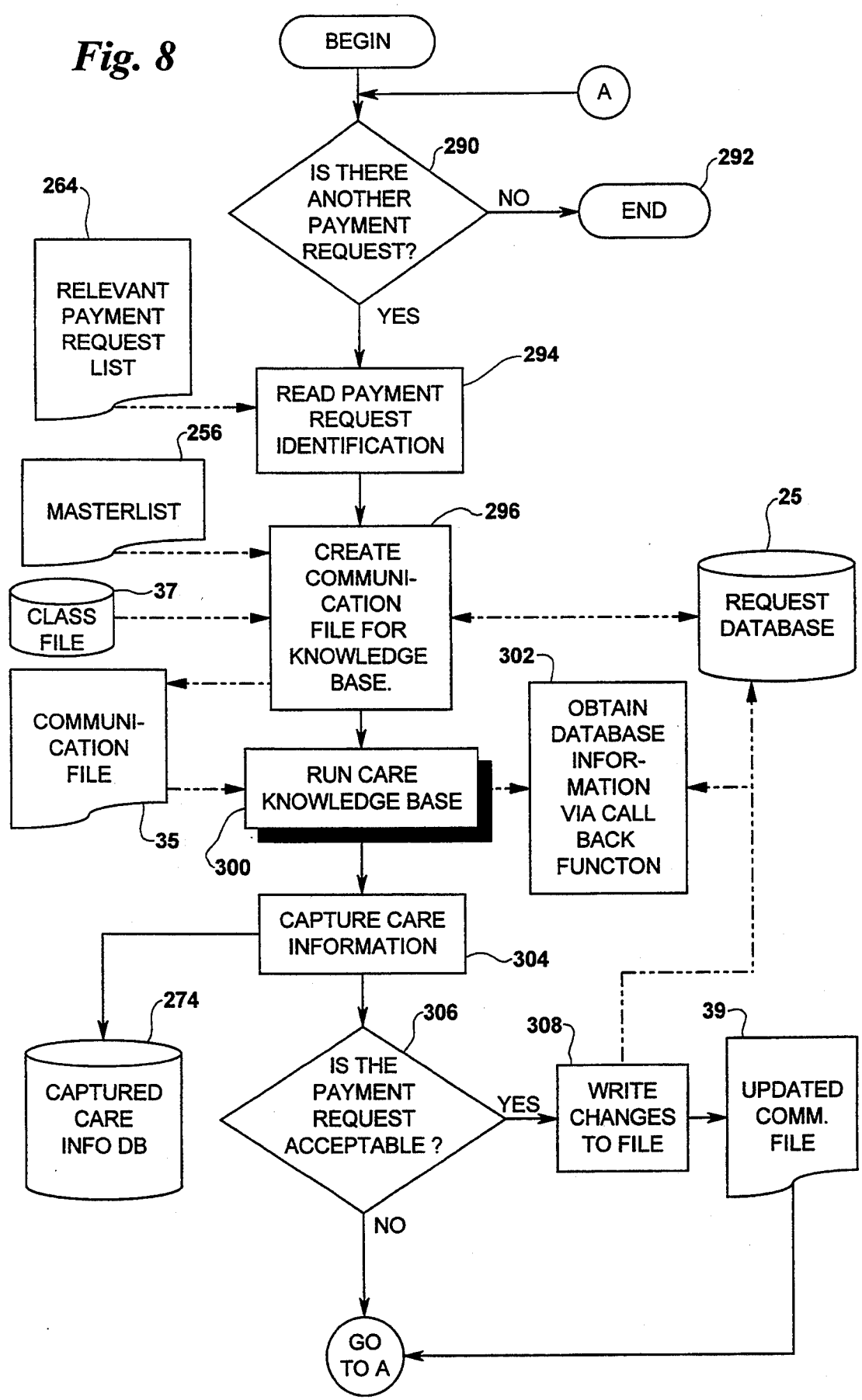
FIG. 8 is a flow chart depicting in greater detail the supervise expert system knowledgebase step of FIG. 6.

FIG. 8 depicts the supervise expert system knowledgebase step 268 of FIG. 6 in greater detail. The supervise expert system knowledgebase step (step 268) uses the relevant payment request list 264 to determine which payment request to process next. The system 20 begins the supervise expert system knowledgebase step 268 by testing whether there are more payment requests to process with the same review code for the current review (step 290). If there are no more payment requests to process for this review, the system 20 returns to begin processing payment requests for another review (step 292).

If there is another payment request to process, the system 20 reads the payment request identification number (step 294). The system 20 then creates a communication file 35 for the expert system knowledgebase 33 (step 296). The communication file 35 provides the expert system knowledgebase 33 with the data for adjudication of a payment request. The communication file 35 includes, at a minimum, the current payment request, information from the Masterlist 256, information from the class file database 37 and relevant historical payment requests from the payment request database 25 as required by the desired review.

The class file database 37 contains class information embodying the hierarchical organization of CPT codes. The CPT organizes procedures into classes based upon the procedure's relation to specific body systems such as the cardiovascular system, digestive system, muscloskeletal system and the like. The class file database 37 contains this organization of CPT procedure codes and is used by the expert system knowledgebase 33 to adjudicate payment requests. In particular, the user-specified rules contained in the expert system knowledgebase 33 are typically structured to relate user-defined adjudication information with the CPT class rather than with the particular procedure code. For example, the user may define a rule that states procedures in the muscloskeletal class are paid according to a particular user-defined formula. The knowledgebase 33 then determines whether or not the particular procedure is in the muscloskeletal class according to the information provided in the class file database 37. The advantage of relating user-defined adjudication information to CPT classes rather than particular procedure codes is that the CPT classes are relatively static while the particular procedure codes are changed frequently.

Next, the system 20 runs the expert system knowledgebase 33 to adjudicate the payment request for that review code (step 300), taking into consideration the type of review, the contents of the current payment request, relevant historical payment requests, the Masterlist 256, the class file database 37 information and the user specified rules for interpreting this information.

If the expert system knowledgebase 33 needs more information before it can make a payment decision, the expert system knowledgebase 33 will ask the supervise expert system knowledgebase process to obtain that information (step 268). For example, based on a characteristic of a particular procedure shown in the Masterlist 256, the expert system knowledgebase 33 may determine it needs more information, or may accept or deny or ignore the payment request. In particular, based on the Masterlist 256, the expert system knowledgebase 33 may know that a particular procedure is a diagnostic procedure. The rules of the expert system knowledgebase 33 tell the expert system 32 that the payer does not permit payment for a physician assisting with a diagnostic procedure so the expert system 32 denies payment for the assistant physician for this procedure. In another example, the expert system knowledgebase 33 may question the supervise expert system knowledgebase step about information contained in a historical payment request to determine the effect of the historical payment request (step 302) on the payment decision for the current payment request.

As the expert system knowledgebase 33 adjudicates the payment request, the system 20 collects and stores the decisions made and reasoning used by the expert system knowledgebase 33 to make the payment decisions (step 304). This captured information is stored in the captured expert system information database 274 to be used in creating the expert system supporting reports 254.

After the expert system knowledgebase 33 completes the adjudication process, the system 20 tests whether the payment request is acceptable (step 306). The payment request is acceptable if the expert system knowledgebase 33 has been able to complete adjudication of the payment request. If the payment request is acceptable, the information reflecting the successful adjudication of the payment request is added or changed to the updated communication file 39 and stored in the payment request database 25(step 308). The updated communication file 39 includes the information in the communication file 35 combined with information reflecting the adjudication decision.

Once the system determines whether the payment request is acceptable or not (step 306), the system 20 tests whether there are more payment requests with the same review code (step 290) and continues the review process (steps 294-308) for any additional payment requests. If there are no more payment requests with the same review code, the system returns (step 292).

Figure 9:
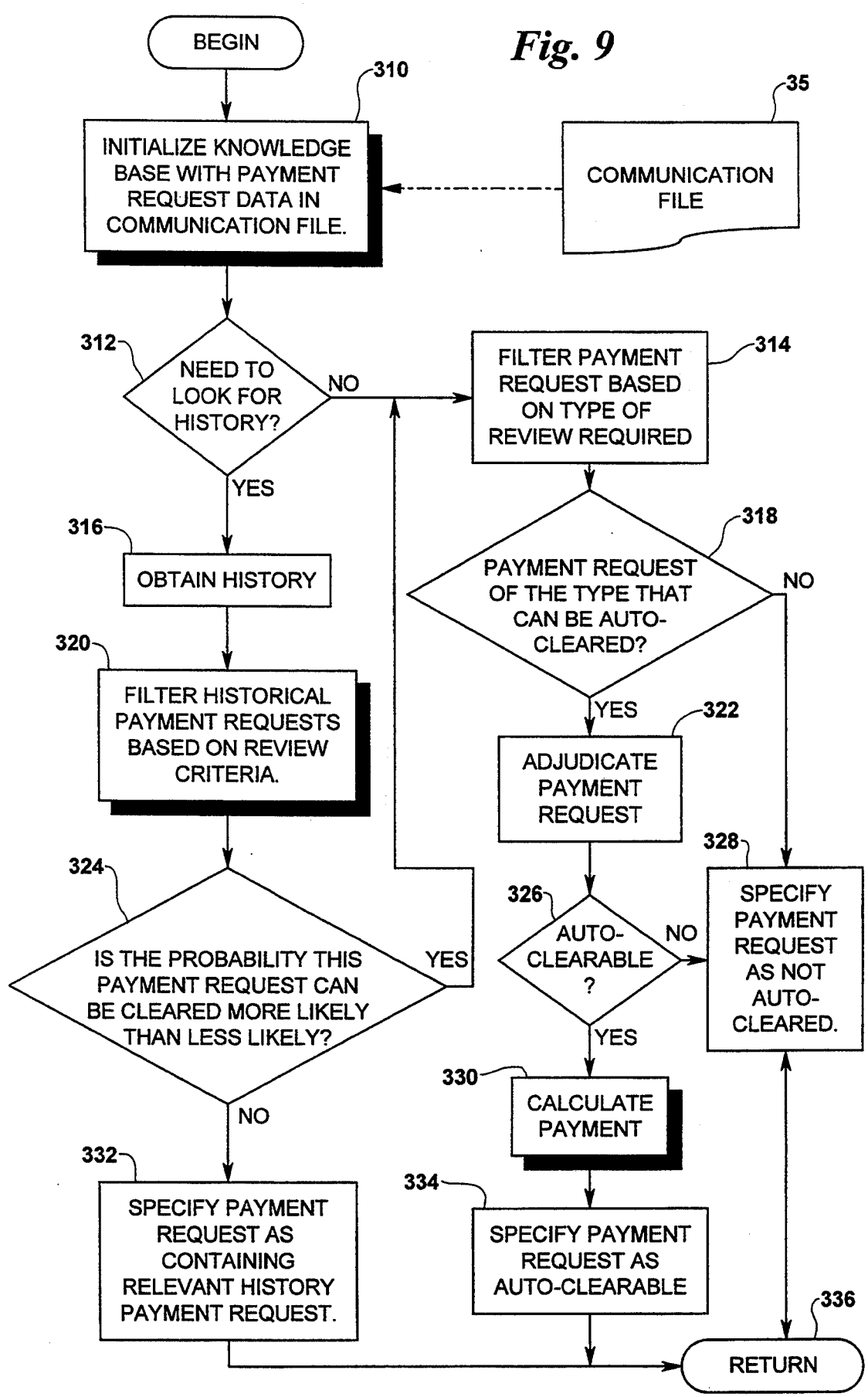
FIG. 9 is a flow chart depicting in greater detail the run expert knowledgebase step of FIG. 8.

FIG. 9 depicts the run expert system knowledgebase step 300 of FIG. 8 in greater detail. The system 20 begins by using the communication file 35 to initialize the expert system knowledgebase 33 and provide the expert system knowledgebase 33 with payment request information (step 310). Next, the system 20 tests whether there is a need to obtain any historical payment request information (step 312). If there is a need, the system 20 obtains the historical payment requests (step 316) and then filters/sorts the historical payment requests so that only the historical payment requests relevant to the current review are present in the communication file 35 (step 320). Relevant historical payment requests are combined with payment request information, class file database 37 information and Masterlist 256 information in the communication file 35.

Once the relevant historical payment requests are obtained, the system 20 tests whether it is more likely than not that the expert system knowledgebase 33 will be able to adjudicate the payment request (step 324). In particular, those skilled in the art will appreciate that, based on the inputs provided to the knowledgebase 33, initial screening of the data can determine the likelihood of the knowledgebase 33 being able to resolve the payment request. If the likelihood of resolving the payment request by expert system knowledgebase 33 is low, the system 20 specifies the current payment request as containing relevant historical payment requests (step 332) and returns (step 336) so the payment request may receive further review by a medical analyst.

If the likelihood of the expert system knowledgebase 33 resolving the payment request is acceptable, the system 20 filters and sorts the payment requests based on the review required (step 314). The system 20 then tests whether the payment request is of the type that can be auto-cleared (i.e., no further review is required) (step 318). If the payment request cannot be auto-cleared, then the system 20 specifies that the payment request is not auto-clearable (step 328) and returns, processing the request as a not auto-clearable payment request (step 336).

If the payment request is of the type that can be auto-cleared, the expert system knowledgebase 33 adjudicates the payment request (step 322).

After the expert system knowledgebase 33 has adjudicated the payment request, the system 20 determines whether, after this further adjudication, the payment request may now be auto-cleared (step 326). If the payment request cannot be auto-cleared, the system 20 specifies that the payment request is not auto-clearable (step 328) and returns to continue processing the request as a not auto-clearable payment request (step 336).

If the payment request can not be auto-cleared, the system 20 calculates the recommended payment for the payment request (step 330), specifies that the payment request is auto-clearable (step 334) and returns to continue processing the request as auto-clearable payment request (step 336).

Figure 10:
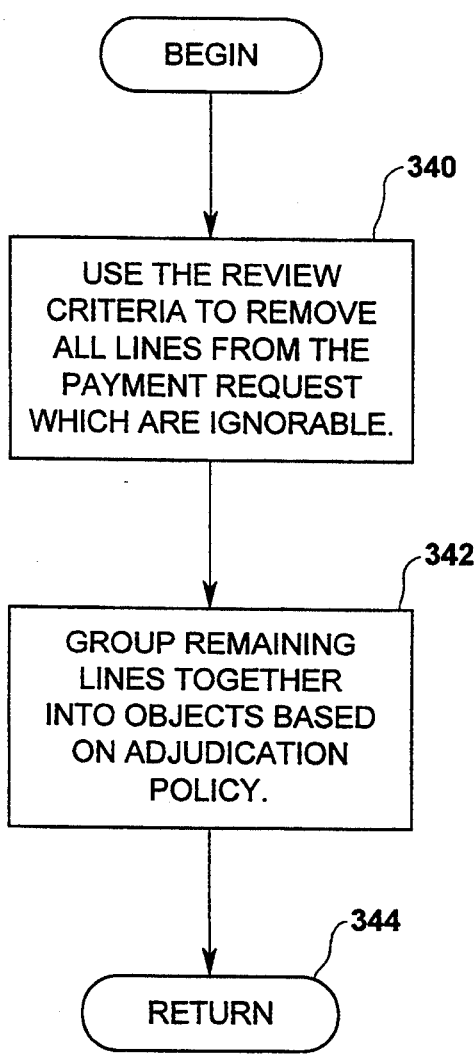
FIG. 10 is a flow chart depicting in greater detail the initialize knowledgebase step of FIG. 9.

FIG. 10 depicts the initialize knowledgebase step 310 of FIG. 9 in greater detail. The initialize knowledgebase 33 step 310 of FIG. 9 begins by removing from the review, all the parts of the payment request which can be ignored in this particular review (step 340).

For example, referring to FIG. 2a, in a multiple surgical review, the payment request 62 for the adenoidectomy procedure alone may be ignored because the adenoidectomy 60 is already included as part of the procedure in the first procedure labelled tonsillectomy/adenoidectomy. After removing ignorable lines from the payment request, the system 20 then groups together the remaining procedures listed on the payment request according to the payer's adjudication policies (step 342) and returns (step 344).

Figure 11:
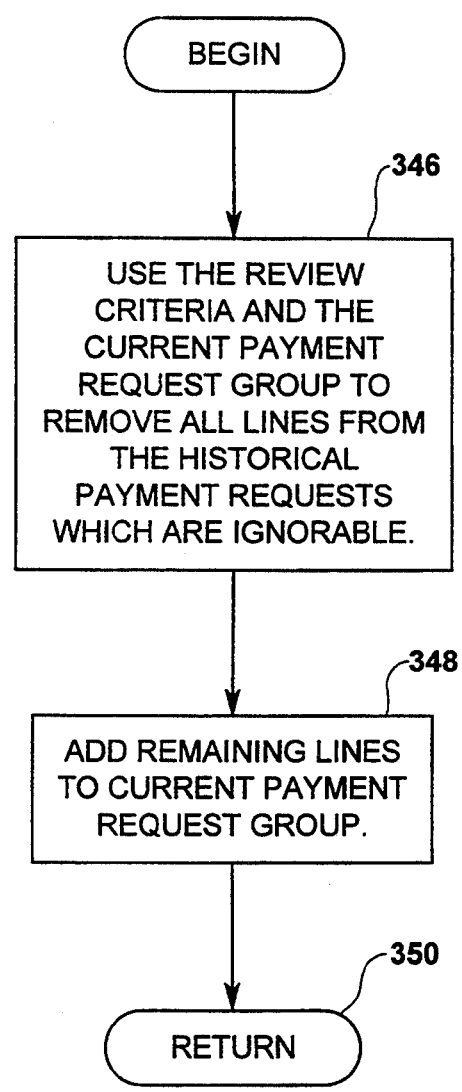
FIG. 11 is a flow chart depicting in greater detail the filter historical payment step of FIG. 9.

FIG. 11 depicts the filter historical payment step 320 of FIG. 9 in greater detail. The filter historical payments step 320 begins with the system 20 examining the relevant historical payment requests and removing from the review all the lines of each payment request which can be ignored in this particular review (step 346).

The system 20 then groups together the remaining lines of each historical payment requests(s) with the current payment request for the review of the current payment request in the context of the prior requests (step 348) and returns (step 350).

The determination of what historical payment requests are relevant is determined by the particular review criteria. For example, when adjudicating a payment request for more than one surgical procedure performed on the same patient on the same day, the relevant historical payment requests are other payment requests for the same patient for the same day. In this example, through there may be many payment requests for the same patient in the payment request database 25, only the payment requests for work performed on the same day as the current payment request are considered relevant. For another example, when adjudicating a payment request for a maternity surgical procedure such as birth by Caesarean section, relevant historical payment requests are those occurring over the past nine months and relating to the pregnancy.

Figure 12:
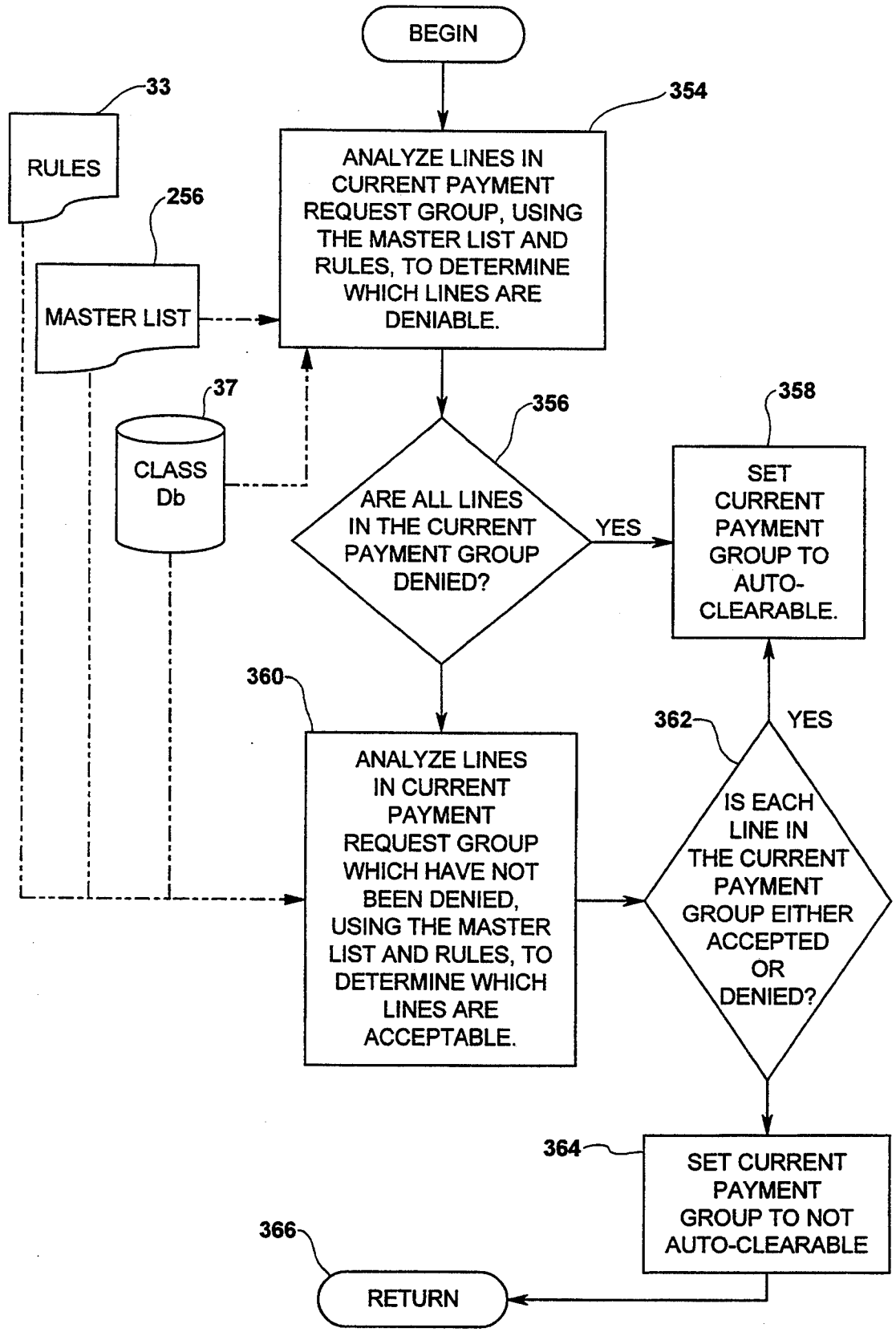
FIG. 12 is a flow chart depicting in greater detail the adjudicate payment step of FIG. 9.

FIG. 12 depicts the adjudicate payment step 322 of FIG. 9 in greater detail. The adjudicate payment step 322 of FIG. 9 begins by analyzing each line of the current payment group to determine which of the individual lines of the payment request group can be denied payment (step 354). The system 20 uses relationships embodied in the Masterlist 256 and the rules contained in the expert system knowledgebase 33 to determine whether to deny the payment request or not.

After analysis, the system 20 then tests whether all the lines in the current payment request have been denied (step 356). If all the lines of the current payment request analyzed for the current review have been denied, then the system 20 sets the current payment group as auto-clearable (step 358) and returns (step 366).

If all of the lines of the current payment request have not been denied, the system 20 analyzes the lines to determine which of the lines are acceptable for payment (step 360). In analyzing the lines for payment acceptability, the system 20 uses relationships embodied in the Masterlist 256 class file database 37 information and the rules contained in the expert system knowledgebase 33 to determine whether to accept the payment request or not.

Next the system 20 tests whether each line in the current payment group has been either accepted or denied (step 362). If each line has not been either accepted or denied, the system 20 specifies the current payment request group as not auto-clearable (step 364) and returns (step 366). If each line in the current payment request group has been either accepted or denied, the system 20 specifies the current payment request group as auto-clearable (step 358) and returns (step 366).

Figure 13:
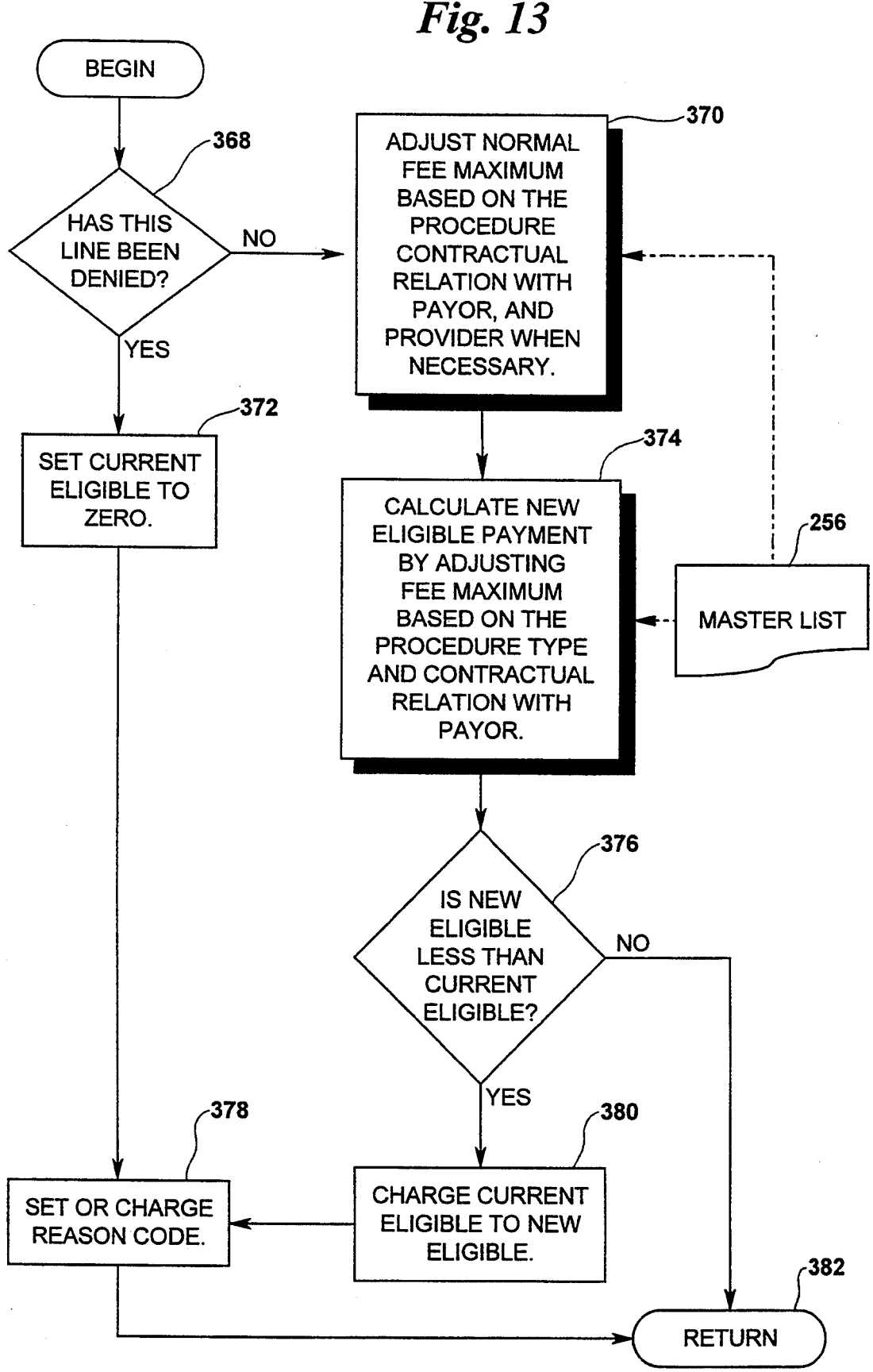
FIG. 13 is a flow chart depicting in greater detail the calculate payment step of FIG. 9.

FIG. 13 depicts the calculate payment step 330 of FIG. 9 in greater detail. The calculate payment step 330 begins with the system 20 testing whether the individual line of the payment request has been denied or not (step 368). If the line has not been denied, the system 20 then adjusts the normal fee maximum paid, called the eligible payment, according to the procedure for which payment is requested, the contractual arrangements between the individual health care providers and the payer (step 370).

The system 20 then calculates the new eligible payment by adjusting the fee maximum based on the procedure type and contractual relationship with the payer and Masterlist 256 information (step 374). Occasionally, when the payer wishes to encourage health care providers to perform a particular procedure, the payer may pay a higher than usual fee for that procedure and the system 20 adjusts for that special situation in step 374.

Next, the system 20 tests whether the new eligible is less than the current eligible payment amount (step 376). If the new eligible payment amount is not less than the current eligible amount, then the system 20 maintains the current eligible amount and returns (step 382). If the new eligible payment amount is less than the current eligible amount, then the system 20 changes the current eligible amount to the new eligible amount (step 380) and sets or changes the reason code to reflect the reasoning for changing or setting the eligible payment amount (step 378) and returns (step 382). The reason code is a code which corresponds to an explanation for changing or setting the eligible payment amount to an amount different from the original eligible payment amount.

If the individual line of the payment request has been denied, the system 20 sets the current eligible payment amount to zero (step 372), sets or changes the reason code (step 378) and returns (step 382).

Figure 14:
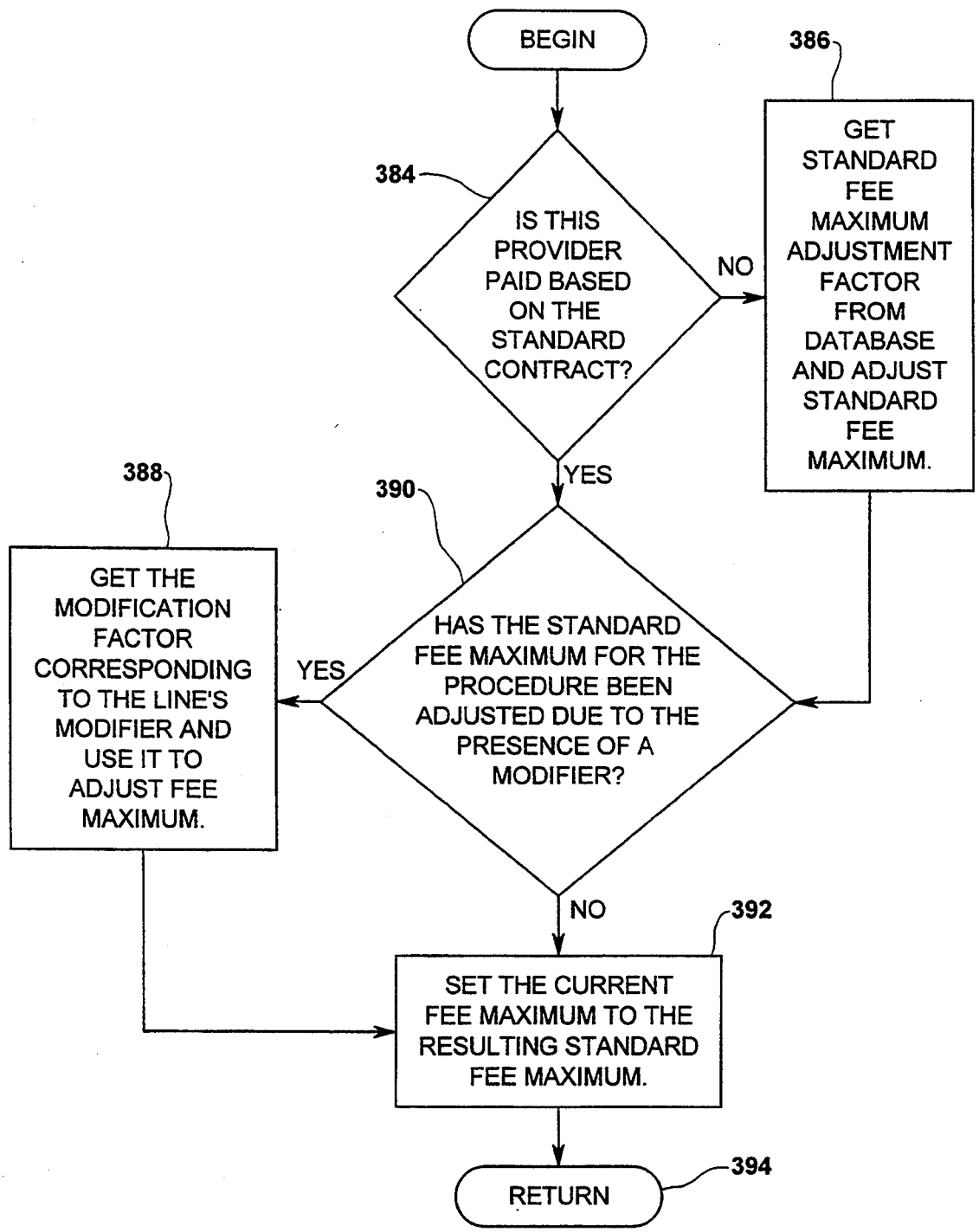
FIG. 14 is a flow chart depicting in greater detail the adjust normal fee maximum step of FIG. 13.

FIG. 14 depicts the adjust normal fee maximum step 370 of FIG. 13 in greater detail. The adjust normal fee maximum step 370 begins by testing whether this health care provider is paid based on the standard contractual arrangements (step 384). If the health care provider is not paid according to the standard contractual arrangements between payers and providers, the system 20 gets the standard maximum fee adjustment factor from the database and adjusts the standard maximum fee (step 386).

Next, the system 20 tests whether the standard fee maximum for the particular procedure for which payment is requested has been adjusted, for example, due to the presence of a modifier (step 390). A modifier is a code which indicates some sort of special situation that may affect the payment amount. For example, a modifier may indicate that the procedure is a bilateral procedure meaning that the operation is performed on both sides of the body such as, for example, when a physician places tubes in each ear on either side of a child's head.

If the standard fee maximum for the procedure has not been adjusted, the system 20 sets the current fee maximum to the standard fee maximum (step 392) and returns (step 394). If the standard fee maximum for the procedure has been adjusted, the system 20 gets the modification factor corresponding to the particular procedure's modifier and adjusts the fee maximum accordingly (step 388). In this instance, the system 20 then sets the current fee maximum to the adjusted standard fee maximum (step 392) and returns (step 394).

Figure 15:
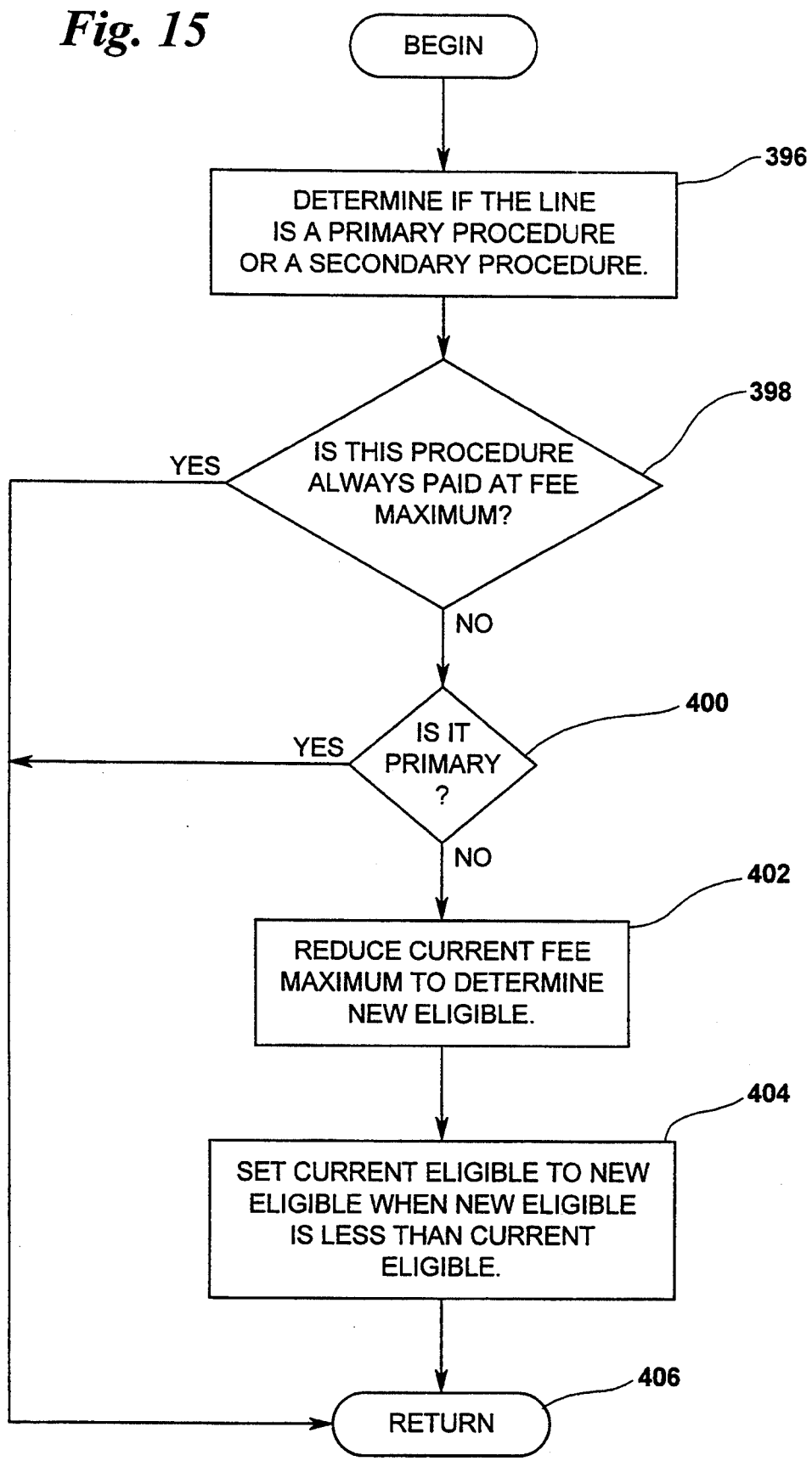
FIG. 15 is a flow chart depicting in greater detail the calculate new eligible payment step of FIG. 13; and, FIG. 16 is an example of a report listing relevant historical payment requests based on the review criteria.

FIG. 15 depicts the calculate new eligible payment step 374 of FIG. 13 in greater detail. The calculate new eligible payment step 374 begins by determining which line is considered a primary procedure and which is a secondary procedure (step 396). The determination of which procedure is considered a primary procedure and which is a secondary procedure has a direct effect on the amount of payment. For example, when there is more than one surgical procedures performed on the same day, the primary procedure is usually the procedure with the highest eligible payment and often is paid in full while the secondary procedure has a smaller eligible and is often adjusted for payment of less than the eligible payment if that procedure was a primary procedure. This policy has the effect of optimizing payment to physicians.

Next the system 20 tests whether the particular procedure for which payment is requested is always paid at fee maximum or not (step 398). If the procedure is not paid at fee maximum, the system 20 tests whether this procedure is the primary procedure (step 400). If the procedure is not the primary procedure, the system 20 reduces the current fee maximum to the new eligible fee maximum (step 402) according to payer contractual arrangements and sets the current eligible fee maximum to the new eligible fee maximum when the new eligible is less than the current eligible fee maximum (step 404) and returns (step 406).

If the procedure is always paid at the fee maximum or if the procedure is the primary procedure, the system returns (step 406).

It will be understood that the payment decisions, relevant historical payment request information and information in expert system supporting reports 254 may be presented in many different ways such as, for example, as printed reports or as displayed on monitors in computer workstations 28. FIG. 16 depicts an example of a report listing relevant historical payment requests for payment requests reviewed for more than one surgical procedure on the same day for the same patient. Such a relevant historical payment request report broadly includes information, such as that in columns which identifying the payment request 500, the date the payment request was received 502, information identifying the patient 504, the date the procedure or service was provided 506, a list identifying relevant historical payment request 508, information identifying the health care provider making the request 510, information indicating whether the payment request is being reviewed by a medical analyst 512 and information indicating that a historical payment request appears on another report 514.

FIG. 17 depicts another example of an expert system supporting report 254, titled the Clear Report, that can be provided to medical analysts. The Clear Report broadly includes, at a minimum, information in fielded columns which identifies the payment request 500, the date the payment request was received 502, information identifying the patient 504, the date the procedure or service was provided 506, a brief description of the type of procedure performed 516, the procedure code and any modifier from the CPT 518, the dollar amount of the payment request 520, the dollar amount of the eligible payment for that procedure 522, the reason code for choosing that eligible amount 524, the dollar amount for a new eligible amount 526 and a corresponding reason code for recommending the new eligible amount 528. The expert system 32 generates the reason codes to provide advice to the medical analysts for recommended disposition of the payment requests. Each of the numerical reason codes corresponds to predetermined descriptions of the reason for recommending that disposition. The predetermined list of reason codes and descriptions are provided by the user based on their past experience in adjudicating payment requests.

APPENDIX A

| | |
|---|---|
| 10000 | starred_code = true.; |
| 10003 | starred_code = true.; |
| 10020 | starred_code = true.; |
| 10040 | starred_code = true.; |
| 10040 | no_cut_reason = excision.; |
| 10060 | starred_code_true.; |
| 10060-10061 | no_cut_reason = debridement\|excision.; |
| 10061 | base_code = "10060".; |
| 10061 | base_code_assoc = only_one.; |
| 10080 | starred_code = true.; |
| 10080-10081 | no _cut_reason = debridement\|excision.; |
| 10081 | base_code_assoc = only_one.; |
| 10081 | base_code = "10080".; |
| 10100 | starred_code = true.; |
| 10101 | base_code = "10100".; |
| 10120 | starred_code = true.; |
| 10120-10121 | no_cut_reason = debridement.; |
| 10121 | base_code = "10120".; |
| 10121 | base_code_assoc = only_one.; |
| 10140 | starred_code = true.; |
| 10140-10141 | no_cut_reason = debriderent.; |
| 10141 | base_code_assoc = only_one.; |
| 10141 | base_code = "10140".; |
| 10160 | starred_code = true.; |
| 10160 | no_cut_reason = debridement.; |
| 10180 | no_cut_reason = debridement.; |
| 11000 | starred_code = true.; |
| 11000-11001 | no_cut_reason = debridement.; |
| 11040-11044 | no_cut_reason = debridement.; |
| 11050 | starred_code = true.; |
| 11050-11052 | no_cut_reason = excision.; |

APPENDIX A-continued

| | |
|---|---|
| 11051-11052 | base_code = "11050".; |
| 11051-11052 | base_code_assoc = only_one.; |
| 11100-11101 | no_cut_reason = diagnostic\|excision.; |
| 11100-11101 | reviewable_code = true.; |
| 11200 | starred_code = true.; |
| 11200-11201 | no_cut_reason = excision.; |
| 11400-11406 | no_cut_reason = excision.; |
| 11420-11426 | no_cut_reason = excision.; |
| 11440-11446 | no_cut_reason = excision.; |
| 11450 | bilateral = 1.00.; |
| 11450-11451 | no_cut_reason = excision.; |
| 11451 | base_code = "11450".; |
| 11451 | bilateral = 1.00.; |
| 11451 | base_code_assoc = only_1.; |
| 11462 | bilateral = 1.00.; |
| 11462-11463 | no_cut_reason = excision.; |
| 11463 | base_code = "11460".; |
| 11463 | base_code_assoc = only_1.; |
| 11470-11471 | no_cut_reason = excision.; |
| 11471 | base_code_assoc = only_1.; |
| 11471 | base_code = "11470".; |
| 11600-11606 | no_cut_reason = excision.; |
| 11620-11626 | no_cut_reason = excision.; |
| 11640-11646 | no_cut_reason = excision.; |
| 11700 | no_cut_reason = debridement.; |
| 11700 | starred_code = true.; |
| 11701 | no_cut_reason = debridement\|adjunct.; |
| 11710 | starred_code = true.; |
| 11710 | no_cut_reason = debridement.; |
| 11711 | no_cut_reason = debridement\|adjunct.; |
| 11730 | starred_code = true.; |
| 11731 | no_cut_reason = sequential.; |
| 11731 | bilateral = 1.00.; |
| 11732 | bilateral = 1.00.; |
| 11732 | no_cut_reason = adjunct\|sequential.; |
| 11750 | bilateral = 0.75.; |
| 11750-11750 | reviewable_code = true.; |
| 11752 | base_code_"11750".; |
| 11752 | bilateral = 0.75.; |
| 11752 | base_code_assoc = only_one.; |
| 11760 | bilateral = 0.75.; |
| 11762 | base_code = 11760". |
| 11762 | bilateral = 0.75.; |
| 11765 | bilateral = 0.75.; |
| 11771-11772 | base_code = "11770".; |
| 11771-11772 | base_code_assoc = only_one.; |
| 11900 | starred_code = true.; |
| 11900-11954 | no_cut_reason = injection.; |
| 11901 | starred_code = true.; |
| 11901 | base_code_assoc = only_one.; |
| 11901 | base_code = "11900".; |
| 11950 | bilateral = 1.00.; |
| 11951 | bilateral = 1.00.; |
| 11952 | bilateral = 1.00.; |
| 11954 | bilateral = 1.00.; |
| 11960 | bilateral = 0.75.; |
| 11960-11960 | reviewable_code = true.; |
| 11970 | bilateral = 6.75.; |
| 11970-11971 | reviewable_code = true.; |
| 11971 | bilateral = 0.75.; |
| 12001 | starred_code = true.; |
| 12001-13300 | no_cut_reason = repair.; |
| 12001-16999 | reviewable_code = true.; |
| 12002 | starred_code = true.; |
| 12002-12007 | base_code = "12001".; |
| 12002-12007 | base_code_assoc = only_one.; |
| 12004 | starred_code = true.; |
| 12011 | starred_code = true.; |
| 12013 | starred_code = true.; |

We claim:

1. In a networked computer processing system including first processor means for executing computer programs and having an associated storage means for storing data and one or more second processor means for executing computer programs, each second processor having an associated storage means for storing data, each of the second processor means being operably connected to the first processor means, a method for processing and adjudicating health care payment requests comprising the steps of:

(a) providing the first processor means with database information stored in the storage means, including:

(a1) a current payment request database having information relating to a plurality of outstanding health care payment requests, each health care payment request having one or more payment request line items corresponding to a specific medical procedure or supply for which payment is being requested;

(a2) a historical payment request database having information relating to a plurality of previously stored health care payment requests;

(a3) a plurality of procedure code list files, each of the procedure code list files having information relating to a certain medical procedure or supply and created according to one or more user-defined characteristics from a predefined complete set of medical procedures and supplies; and (a4) a class file having information relating to classification of the predefined complete set of medical procedures and supplies and created according to a predefined set of body systems;

(b) providing each of the second processor means with an expert-based computer program including a set of user-defined rules and knowledge database information for the expert-based computer program stored in the storage means of the second processor means;

(c) using the first processor means to perform the steps of:

(c1) creating a payment request list from the current request database by selecting one or more payment request line items in response to a user-specified review code;

(c2) creating a master list file by logically combining the plurality of procedure code list files with each other in response to the user-specified review code;

(c3) for each payment request line item in the payment request list, creating a record in a communication file containing:

(c31) information from the current payment request database relating to the payment request line item;

(c32) information from the historical payment request database relating to a subset of relevant payment request line items selected from the historical payment request database;

(c33) information from the master list file relating to the procedure or supply for which payment is being requested by the payment request line item; and (c34) information from the class file relating to the procedure or supply for which payment is being requested by the payment request line item; and (c4) communicating the communication file to one or more of the second processor means;

(d) receiving the communication file and storing the communication file in the storage means of at least one of the second processor means and executing the expert-based computer program on the second processor means to perform the following steps for each payment request line item in the communication file:

(d2) using the set of user-defined rules and knowledge database information to determine the consistency of 'the payment request line item as compared to the information from the subset of relevant payment request line items selected from the historical payment database;

(d2) using the set of user-defined rules and knowledge database information and the information from the master list file and the class file to determine the validity of the payment request line item;

(d3) making a decision on whether to pay the payment request line item based upon the consistency and validity of the payment request line item and the set of user-defined rules and knowledge database information;

(d4) if the payment request line item is to be paid, determining an amount of a payment for the payment request line item based upon the consistency and validity of the payment request line item and the set of user-defined rules and knowledge database information; and (d5) generating an updated communication file to be communicated to the first processor means, the updated communication file including:

(d51) the decision on whether to pay each payment request line item in the communication file;

(d52) the amount of the payment for each payment request line item in the communication file that is to be paid; and (d53) one or more items of coded information representing why the payment request line item is not to be paid for each payment request line item that is not to be paid; and (e) receiving the updated communication file from each of the one or more second processor means and using the first processor means to update the current request database to generate the historical request database.

2. The method of claim 1 wherein the current request database and the historical request database are stored as part of a single payment request database.

3. The method of claim 1, further comprising the steps of:

(f) using the first processor means to analyze the updated communication file in response to a user request and generate one or more pre-defined reports summarizing the payment request line items.

4. An apparatus for processing and adjudicating health care payment requests on a networked computer processing system, the apparatus comprising:

first processor means for executing computer programs and having an associated storage means for storing data, the data including:

a current payment request database having information relating to a plurality of outstanding health care payment requests, each health care payment request having one or more payment request line items corresponding to a specific medical procedure or supply for which payment is being requested;

a historical payment request database having information relating to a plurality of previously stored health care payment requests;

a plurality of procedure code list files, each of the procedure code list files having information relating to a certain medical procedures or supplies and created according to one or more used-defined characteristics from a predefined complete set of medical procedures and supplies; and a class file having information relating to classification of the predefined complete set of medical procedures and supplies and created according to a predefined set of body systems; and one or more second processor means for executing computer programs, each second processor having an associated storage means for storing data, each of the second processor means being operably connected to the first processor means and being provided with an expert-based computer program including a set of user-defined rules and knowledge database information for the expert-based computer program stored in the storage means;

the first processor means including:

means for creating a payment request list from the current request database by selecting payment request line items in response to a user-specified review code;

means for creating a master list file by logically combining the plurality of procedure code list files with each other in response to the user-specified review code;

means for creating a record in a communication file for each payment request line item in the payment request list, said record containing:

information from the current payment request database relating to the payment request line item;

information from the historical payment request database relating to a subset of relevant payment request line items selected from the historical payment database;

information from the master list file relating to the procedure or supply for which payment is being requested by the payment request line item; and information from the class file relating to the procedure or supply for which payment is being requested by the payment request line item; and means for communicating the communication file to one or more of the second processor means;

the one or more second processor means, each including means for receiving the communication file and storing the communication file in the storage means of the second processor means and means for executing the expert-based computer program on the second processor means for each payment request line item in the communication file, including:

means for using the set of user-defined rules and knowledge database information to determine the consistency of the payment request line item as compared to the information from the subset of relevant payment request line items selected from the historical payment database;

means for using the set of user-defined rules and knowledge database information and the information from the master list file and the class file to determine the validity of the payment request line item;

means for making a decision on whether to pay the payment request line item based upon the consistency and validity of the payment request line item and the set of user-defined rules and knowledge database information;

if the payment request line item is to be paid, means for determining an amount of a payment for the payment request line item based upon the consistency and validity of the payment request line item and the set of user-defined rules and knowledge database information; and means for generating the updated communication file to be communicated to the first processor means, the updated communication file including:

coded information representing the decision on whether to pay each payment request line item in the communication file;

coded information representing the amount of the payment for each payment request line item in the communication file that is to be paid; and coded information representing why the payment request line item is not to be paid for each payment request line item that is not to be paid.

5. The method of claim 3, wherein the updated communication file further includes (d54) workload information representing the assignment of a payment request to a medical analyst for further review.

6. The method of claim 3, wherein the first processor means further includes (c5) means for receiving the updated communication file from the one or more second processor means and updating the current request database to generate the historical request database.

7. In a networked computer processing system, a method for using a plurality of historical payment requests stored in a database in the networked computer processing system in the adjudication of one or more current payment requests, the method comprising the computer-implemented steps of:

(a) identifying one or more initial selection criteria to be used for selecting a set of the relevant historical payment requests;

(b) creating the set of one or more relevant historical payment requests in response to one or more of the initial selection criteria by selecting the historical payment requests that match the initial selection criteria;

(c) identifying one or more screening criteria to screen the set of relevant historical payment requests selected in (b) for pertinent information;

(d) collecting information from the set of relevant historical payment requests selected in step (b) using the screening criteria to sort the historical payment requests containing information that matches the screening criteria and storing said information in a communications file;

(e) sorting information stored in the communications file according to predetermined presentation order.

8. The method of claim 7 wherein the initial selection criteria is identified according to a user-defined review code criteria.

9. The method of claim 7 wherein the predetermined presentation order is based on a user-defined review code criteria.

10. The method of claim 7 further comprising the computer-implemented steps of:

(f) storing the sorted communications file; and (g) outputting the stored communication file for analysis.

* * * * *

UNITED STATES PATENT AND TRADEMARK OFFICE
CERTIFICATE OF CORRECTION

PATENT NO. : 5,359,509

DATED : October 25, 1994

INVENTOR(S) : John P. Little et al.

It is certified that error appears in the above-identified patent and that said Letters Patent is hereby corrected as shown below:

Column 6, line 24, delete "62,64,66" and substitute therefor -- 62, 64, 66 --.

Column 8, line 55, delete "( a" and substitute therefor -- (a --.

Column 10, line 41, delete "42,44," and substitute therefor -- 42, 44 --.

Column 11, line 61, delete "'the" and substitute therefor -- the --.

Column 12, lines 33-34, delete "user -specified" and substitute therefor -- user-specified --.

Column 13, line 26, delete "25(step" and substitute therefor -- 25 (step --.

Column 14, line 60, delete "through" and substitute therefor -- though --.

Column 17, Appendix A, line 6, delete "code__true.;" and substitute therefor -- code = true.; --.

Column 17, Appendix A, line 21, delete "debriderent.;" and substitute therefor -- debridement --.

Column 20, line 1, delete "(d2)" and substitute therefor -- (d1) --.

Column 20, line 3, delete "'the" and substitute therefor -- the --.

UNITED STATES PATENT AND TRADEMARK OFFICE
CERTIFICATE OF CORRECTION

PATENT NO. : 5,359,509
DATED : October 25, 1994
INVENTOR(S) : John P. Little et al.

It is certified that error appears in the above-indentified patent and that said Letters Patent is hereby corrected as shown below:

Column 22, line 20, delete "include" and substitute therefor -- include: --.

Column 22, line 25, delete "include" and substitute therefor -- include: --.

Signed and Sealed this

Eighteenth Day of April, 1995

Attest:

BRUCE LEHMAN

Attesting Officer

Commissioner of Patents and Trademarks